US012219877B2

(12) United States Patent
Han et al.

(10) Patent No.: US 12,219,877 B2
(45) Date of Patent: Feb. 4, 2025

(54) MULTI-ELEMENT PIEZO SENSORS FOR PHYSIOLOGICAL MEASUREMENTS

(71) Applicant: Apple Inc., Cupertino, CA (US)

(72) Inventors: Chin San Han, Mountain View, CA (US); German A. Alvarez, San Jose, CA (US); Santiago Quijano, San Jose, CA (US); Stuart W. Wenzel, San Carlos, CA (US)

(73) Assignee: Apple Inc., Cupertino, CA (US)

( * ) Notice: Subject to any disclaimer, the term of this patent is extended or adjusted under 35 U.S.C. 154(b) by 187 days.

(21) Appl. No.: 17/730,841

(22) Filed: Apr. 27, 2022

(65) Prior Publication Data

US 2022/0254984 A1     Aug. 11, 2022

Related U.S. Application Data

(62) Division of application No. 15/986,643, filed on May 22, 2018, now Pat. No. 11,349,063.

(Continued)

(51) Int. Cl.
    *H01L 41/113*     (2006.01)
    *A61B 5/00*     (2006.01)
    (Continued)

(52) U.S. Cl.
    CPC ......... *H10N 30/302* (2023.02); *A61B 5/1126* (2013.01); *A61B 5/4806* (2013.01);
    (Continued)

(58) Field of Classification Search
    CPC .... H10N 30/302; H10N 30/508; H10N 30/87; H10N 30/1051
    See application file for complete search history.

(56) References Cited

U.S. PATENT DOCUMENTS

| | | | |
|---|---|---|---|
| 3,816,774 A | 6/1974 | Ohnuki | |
| 4,056,742 A | 11/1977 | Tibbetts | |

(Continued)

FOREIGN PATENT DOCUMENTS

| | | |
|---|---|---|
| AU | PN304895 | 5/1995 |
| CN | 1795815 | 7/2006 |

(Continued)

OTHER PUBLICATIONS

Bischoff, "Quantified Sleep: A New Gadget From China Wants to Get in Bed With You," located at https://www.techinasia.com/quantified-sleep-gadget-china-bed/, accessed on Nov. 27, 2014, pp. 1-6.

(Continued)

*Primary Examiner* — Bryan P Gordon
(74) *Attorney, Agent, or Firm* — Brownstein Hyatt Farber Schreck, LLP

(57) ABSTRACT

Disclosed herein are monitoring systems and sensors for physiological measurements. The sensors can be multi-element piezo sensors capable of generating multiple electrical signals, whereby the monitoring systems can receive the multiple electrical signals to analyze the user's vital signs along multiple regions of the user's body. In some examples, the piezo sensor can include one or more corrugations, such as peaks and valleys, to create localized regions with increased mechanical response to force. The sensitivity and resolution of the piezo sensor can be enhanced by further locating electrode sections at the corrugations, where the electrode sections can be electrically isolated and independently operable from other electrode sections. Traces electrically connecting an electrode section (Continued)

to, e.g., an off-panel controller can be routed over and/or around other electrode sections by including an insulator to electrically insulate from the other electrode sections, or by using vias to route through one or more layers.

17 Claims, 13 Drawing Sheets

Related U.S. Application Data

(60) Provisional application No. 62/509,657, filed on May 22, 2017.

(51) Int. Cl.
| | | |
|---|---|---|
| *A61B 5/11* | (2006.01) | |
| *G01L 1/16* | (2006.01) | |
| *G01L 1/20* | (2006.01) | |
| *H10N 30/00* | (2023.01) | |
| *H10N 30/30* | (2023.01) | |
| *H10N 30/50* | (2023.01) | |
| *H10N 30/87* | (2023.01) | |
| *A61B 5/0205* | (2006.01) | |

(52) U.S. Cl.
CPC ............ *A61B 5/6892* (2013.01); *A61B 5/742* (2013.01); *G01L 1/16* (2013.01); *G01L 1/205* (2013.01); *H10N 30/508* (2023.02); *H10N 30/704* (2024.05); *H10N 30/87* (2023.02); *A61B 5/0205* (2013.01); *A61B 5/02055* (2013.01); *A61B 5/6802* (2013.01); *A61B 2560/0252* (2013.01); *A61B 2560/0462* (2013.01); *A61B 2562/04* (2013.01); *A61B 2562/06* (2013.01)

(56) References Cited

U.S. PATENT DOCUMENTS

| | | | |
|---|---|---|---|
| 5,479,939 A | 1/1996 | Ogino | |
| 5,483,261 A | 1/1996 | Yasutake | |
| 5,488,204 A | 1/1996 | Mead et al. | |
| 5,571,973 A | 11/1996 | Taylot | |
| 5,825,352 A | 10/1998 | Bisset et al. | |
| 5,835,079 A | 11/1998 | Shieh | |
| 5,880,411 A | 3/1999 | Gillespie et al. | |
| 6,107,726 A | 8/2000 | Near | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,425,861 B1 | 7/2002 | Haberland et al. | |
| 6,468,234 B1 | 10/2002 | Van der Loos et al. | |
| 6,646,556 B1 | 11/2003 | Smith | |
| 6,690,387 B2 | 2/2004 | Zimmerman et al. | |
| 6,833,656 B2 | 12/2004 | Hooley et al. | |
| 7,015,894 B2 | 3/2006 | Morohoshi | |
| 7,164,941 B2 | 1/2007 | Misczynski et al. | |
| 7,166,952 B2 | 1/2007 | Topliss et al. | |
| 7,184,064 B2 | 2/2007 | Zimmerman et al. | |
| 7,351,206 B2 | 4/2008 | Suzuki et al. | |
| 7,396,331 B2 | 7/2008 | Mack et al. | |
| 7,427,270 B2 | 9/2008 | Izumi et al. | |
| 7,442,107 B1 | 10/2008 | Ueda et al. | |
| 7,486,004 B2 | 2/2009 | Allan et al. | |
| 7,652,581 B2 | 1/2010 | Gentry et al. | |
| 7,654,948 B2 | 2/2010 | Kaplan et al. | |
| 7,656,299 B2 | 2/2010 | Gentry et al. | |
| 7,663,607 B2 | 2/2010 | Hotelling et al. | |
| 7,717,848 B2 | 5/2010 | Heruth et al. | |
| 8,002,553 B2 | 8/2011 | Hallestad et al. | |
| 8,003,982 B2 | 8/2011 | Wang et al. | |
| 8,161,826 B1 | 4/2012 | Taylor | |
| 8,262,582 B2 | 9/2012 | Kortelainen | |
| 8,348,840 B2 | 1/2013 | Heit et al. | |
| 8,355,769 B2 | 1/2013 | Westbrook et al. | |
| 8,398,538 B2 | 3/2013 | Dothie et al. | |
| 8,406,438 B2 | 3/2013 | Ihl et al. | |
| 8,479,122 B2 | 7/2013 | Hotelling et al. | |
| 8,532,737 B2 | 9/2013 | Cervantes | |
| 8,585,607 B2 | 11/2013 | Klap et al. | |
| 8,608,655 B2 | 12/2013 | Izumi | |
| 8,611,828 B2 | 12/2013 | Richter et al. | |
| 8,627,716 B2 | 1/2014 | Son | |
| 8,698,511 B2 | 4/2014 | Wendt et al. | |
| 8,768,520 B2 | 7/2014 | Oexman et al. | |
| 8,870,764 B2 | 10/2014 | Rubin | |
| 9,119,566 B2 | 9/2015 | Sakai et al. | |
| 9,247,831 B2 | 2/2016 | Miles et al. | |
| 9,310,779 B2 | 4/2016 | Huh et al. | |
| 9,314,583 B2 | 4/2016 | Gavish | |
| 9,344,546 B2 | 5/2016 | Choudhary et al. | |
| 9,345,404 B2 | 5/2016 | Proud | |
| 9,478,728 B2 | 10/2016 | Capobianco et al. | |
| 9,498,137 B2 | 11/2016 | Kovacs | |
| 9,592,005 B2 | 3/2017 | Oakhill | |
| 9,596,998 B2 | 3/2017 | Muehlsteff et al. | |
| 9,649,043 B2 | 5/2017 | Meftah et al. | |
| 9,693,696 B2 | 7/2017 | Kovacs et al. | |
| 9,750,415 B2 | 9/2017 | Breslow et al. | |
| 9,788,791 B2 | 10/2017 | Brauers et al. | |
| 9,808,202 B2 | 11/2017 | Wu et al. | |
| 9,814,410 B2 | 11/2017 | Kostic et al. | |
| 9,883,809 B2 | 2/2018 | Klap et al. | |
| 9,981,420 B2 | 5/2018 | Benaissa et al. | |
| 10,004,454 B2 | 6/2018 | Krans et al. | |
| 10,136,853 B2 | 11/2018 | Heinrich et al. | |
| 10,149,549 B2 | 12/2018 | Erko et al. | |
| 10,278,638 B2 | 5/2019 | Dusanter et al. | |
| 10,300,230 B2 | 5/2019 | Flower et al. | |
| 10,368,799 B2 | 8/2019 | Sannholm et al. | |
| 10,376,155 B2 | 8/2019 | Yang et al. | |
| 10,376,214 B2 | 8/2019 | Hayes et al. | |
| 10,463,300 B2 | 11/2019 | Kahn et al. | |
| 10,512,432 B2 | 12/2019 | Shahparnia et al. | |
| 10,610,153 B2 | 4/2020 | Auphan et al. | |
| 11,275,405 B2 | 3/2022 | Hotelling | |
| 11,311,197 B2 | 4/2022 | Yang et al. | |
| 11,918,381 B2 | 3/2024 | Shahparnia et al. | |
| 2005/0257822 A1 | 11/2005 | Smith et al. | |
| 2007/0118054 A1 | 5/2007 | Pinhas et al. | |
| 2008/0169931 A1* | 7/2008 | Gentry ................. A61B 5/1117 600/300 |
| 2009/0121826 A1 | 5/2009 | Song et al. | |
| 2010/0246862 A1* | 9/2010 | Ihl ......................... F16F 15/005 310/331 |
| 2010/0331632 A1 | 12/2010 | Chou | |
| 2011/0230790 A1 | 9/2011 | Kozlov | |
| 2012/0092171 A1 | 4/2012 | Hwang et al. | |
| 2012/0283979 A1 | 11/2012 | Bruekers et al. | |
| 2013/0030257 A1 | 1/2013 | Nakata et al. | |
| 2013/0245502 A1 | 9/2013 | Lange et al. | |
| 2013/0261404 A1 | 10/2013 | Sato et al. | |
| 2014/0039351 A1 | 2/2014 | Mix et al. | |
| 2014/0213878 A1 | 7/2014 | Banet et al. | |
| 2014/0275829 A1 | 9/2014 | Berezhnyy et al. | |
| 2014/0276245 A1 | 9/2014 | Tsutsumi et al. | |
| 2014/0288385 A1 | 9/2014 | Amurthur et al. | |
| 2015/0011899 A1 | 1/2015 | Shigeto et al. | |
| 2016/0038035 A1 | 2/2016 | Tseng | |
| 2016/0106339 A1 | 4/2016 | Behzadi et al. | |
| 2016/0136385 A1 | 5/2016 | Scorcioni | |
| 2016/0157780 A1 | 6/2016 | Rimminen et al. | |
| 2018/0028111 A1 | 2/2018 | Waris et al. | |
| 2018/0337325 A1 | 11/2018 | Han et al. | |
| 2020/0107785 A1* | 4/2020 | Shahparnia ............ A61B 5/282 |
| 2021/0041287 A1* | 2/2021 | Rimminen ............ H10N 30/302 |
| 2022/0254984 A1* | 8/2022 | Han ..................... A61B 5/6892 |

(56) References Cited

U.S. PATENT DOCUMENTS

2022/0330893 A1   10/2022  Shahparnia et al.
2022/0346656 A1*  11/2022  Smits .................. A61B 5/1036

FOREIGN PATENT DOCUMENTS

| | | |
|---|---|---|
| CN | 1809315 | 7/2006 |
| CN | 101095612 | 1/2008 |
| CN | 101188969 | 5/2008 |
| CN | 101212354 | 7/2008 |
| CN | 101896120 | 11/2010 |
| CN | 101977544 | 2/2011 |
| CN | 102274009 | 12/2011 |
| CN | 102283654 | 12/2011 |
| CN | 102300499 | 12/2011 |
| CN | 102579020 | 7/2012 |
| CN | 103635134 | 3/2014 |
| CN | 104239415 | 12/2014 |
| CN | 105705093 | 6/2016 |
| CN | 105723307 | 6/2016 |
| CN | 106037140 | 10/2016 |
| DE | 102010063385 | 6/2012 |
| EP | 2278507 | 1/2011 |
| EP | 2301429 | 3/2011 |
| EP | 2644087 | 10/2013 |
| EP | 2432391 | 2/2014 |
| EP | 2783725 | 10/2014 |
| EP | 1890594 | 11/2014 |
| EP | 2870914 | 5/2015 |
| EP | 2976993 | 1/2016 |
| JP | 63016237 | 1/1988 |
| JP | 2000163031 | 6/2000 |
| JP | 2002342033 | 11/2002 |
| JP | 2004113618 | 4/2004 |
| JP | 2008082952 | 4/2008 |
| JP | 2008183181 | 8/2008 |
| JP | 2009233027 | 10/2009 |
| JP | 2012170471 | 9/2012 |
| TW | 2004058803 | 4/2004 |
| WO | WO 05/043443 | 5/2005 |
| WO | WO 06/131855 | 12/2006 |
| WO | WO 11/020299 | 2/2011 |
| WO | WO 12/122002 | 9/2012 |
| WO | WO 13/179189 | 12/2013 |
| WO | WO 14/151577 | 9/2014 |
| WO | WO 15/008285 | 1/2015 |
| WO | WO 15/075692 | 5/2015 |
| WO | WO 16/087709 | 6/2016 |
| WO | WO 16/120518 | 8/2016 |
| WO | WO 16/124817 | 8/2016 |
| WO | WO 18/217585 | 11/2018 |

OTHER PUBLICATIONS

Dagdeviren et al., "Recent Progress in Flexible and Stretchable Piezoelectric Devices for Mechanical Energy Harvesting, Sensing and Actuation," *Extreme Mechanics Letters*, Dec. 1, 2016, vol. 9, pp. 269-281.

Feng et al., "Stretchable Ferroelectric Nanoribbons with Wavy Configurations on Elastomeric Substrates," *ACS NANO*, Mar. 23, 2011, vol. 5, No. 4, pp. 3326-3332, p. 3329, col. 1, paragraph 2 to col. 2, paragraph 1, figure 3.

Kortelainen et al. (Jun. 20-22, 2007). "PCA Model for Recording Respiration and Posture with Multichannel BCG Sensor in Bed Mattress," presented at the 4th pHealth Conference, Porto Carras, Greece, pp. 1-5.

Kortelainen et al. (May 2010). "Sleep Staging Based on Signals Acquired Through Bed Sensor," *IEEE Transactions on Information Technology in Biomedicine*, vol. 14, No. 3, pp. 776-785.

Lee et al. (Apr. 1985). "A Multi-Touch Three Dimensional Touch-Sensitive Tablet," Proceedings of CHI: ACM Conference on Human Factors in Computing Systems, pp. 21-25.

Paalasmaa (2014). "Monitoring Sleep with Force Sensor Measurement," University of Helsinki, Department of Computer Science, Series of Publication A, Report A—Feb. 2014, 69 pages.

Paalasmaa et al. (Aug. 28, 2012) "Unobtrusive Online Monitoring of Sleep at Home," Conference Proceeding Article, 34th Annual International Conference of the IEEE EMBS, p. 3784-3788.

Rubine (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Song et al. (Oct. 15, 2014). "Health Sensing by Wearable Sensors and Mobile Phones: A Survey," Conference Proceedings Article of the 16th International Conference on e-Health Networking, Applications and Services (Healthcom), p. 453-459.

Tikotzky et al., "Sleep and physical growth in infants during the first 6 months," *J. Sleep Res.*, 2010, vol. 19, pp. 103-110.

Westerman (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Zeng et al., "Effects of Obstructive Sleep Apnea-Hypopnea Syndrome (OSAHS) on Height and Weight of Children," *Journal of Clinical Otorhinolaryngology Head and Neck Surgery*, Apr. 2013, vol. 27, No. 4, pp. 210-211.

\* cited by examiner

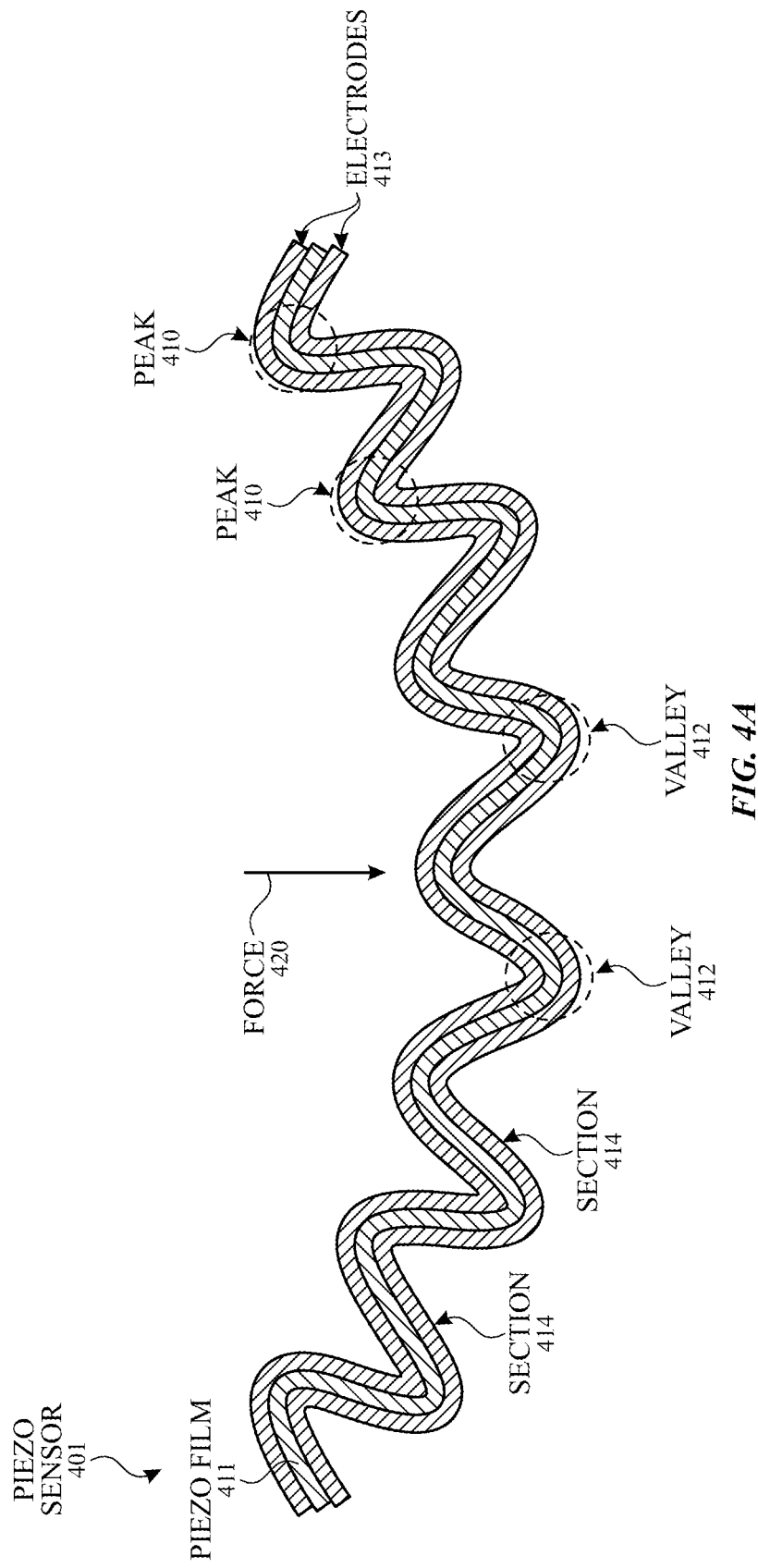

MULTI-ELEMENT PIEZO SENSORS FOR PHYSIOLOGICAL MEASUREMENTS

CROSS REFERENCE TO RELATED APPLICATIONS

This application is a division of U.S. patent application Ser. No. 15/986,643, filed May 22, 2018, which claims the benefit of U.S. Provisional Patent Application No. 62/509,657, filed on May 22, 2017, which are hereby incorporated by reference in their entirety as if fully disclosed herein.

FIELD OF THE DISCLOSURE

This relates generally to monitoring systems and sensors for measuring physiological measurements.

BACKGROUND OF THE DISCLOSURE

Traditionally, monitoring a user's sleep and/or measuring the user's vital signs required expensive and bulky equipment. Some systems require that the monitoring be performed away from home in a medical facility and/or require the equipment to attach to or directly contact the person, which can lead to discomfort and can lead to inaccurate analysis due to disruption of the user's sleep. Some systems can be more user-friendly by way of portability, indirect contact, etc., but these systems are configured to determine the vital signs based on one type of measurement, signal, and/or mode of operation. With a single type of measurement, signal, and/or mode of operation, the sensitivity of these systems can lead to inaccurate and/or insufficient information, thereby rendering any analysis regarding the user's sleep and vital signs ineffective.

SUMMARY OF THE DISCLOSURE

Disclosed herein are monitoring systems and sensors for physiological measurements. The sensors can be multi-element piezo sensors capable of generating multiple electrical signals, whereby the monitoring systems can receive the multiple electrical signals to analyze the user's vital signs along multiple regions of the user's body. In some examples, the piezo sensor can include one or more corrugations, such as peaks and valleys, to create localized regions with increased mechanical response (e.g., sensitivity) to force. The sensitivity and resolution of the piezo sensor can be enhanced by further locating electrode sections at the corrugations, where the electrode sections can be electrically isolated and independently operable from other electrode sections. Traces electrically connecting an electrode section to, e.g., an off-panel controller can be routed over and/or around other electrode sections by including an insulator to electrically insulate from the other electrode sections, or by using vias to route through one or more layers. The multi-element piezo sensor can include multiple piezo films and multiple pairs of electrodes (and/or electrode sections).

Examples of the disclosure also include piezo sensors having multiple piezo film elements, where the force (e.g., stress) can be concentrated onto the piezo film elements. Each piezo film element can be structurally and electrically isolated from other piezo film elements. Force concentration can be performed by configuring one or more intermediate layers to have a tapered profile, including one or more structures to transfer the force to the piezo film elements, configuring one or more intermediate layers to have regions of different force concentration, or a combination thereof. Examples of the disclosure further include piezo sensors configured for converting one type of force into another type of force by Poisson conversion.

BRIEF DESCRIPTION OF THE DRAWINGS

FIG. 4A illustrates a cross-sectional view of an exemplary piezo sensor including corrugations according to examples of the disclosure.

DETAILED DESCRIPTION

Figure 1:
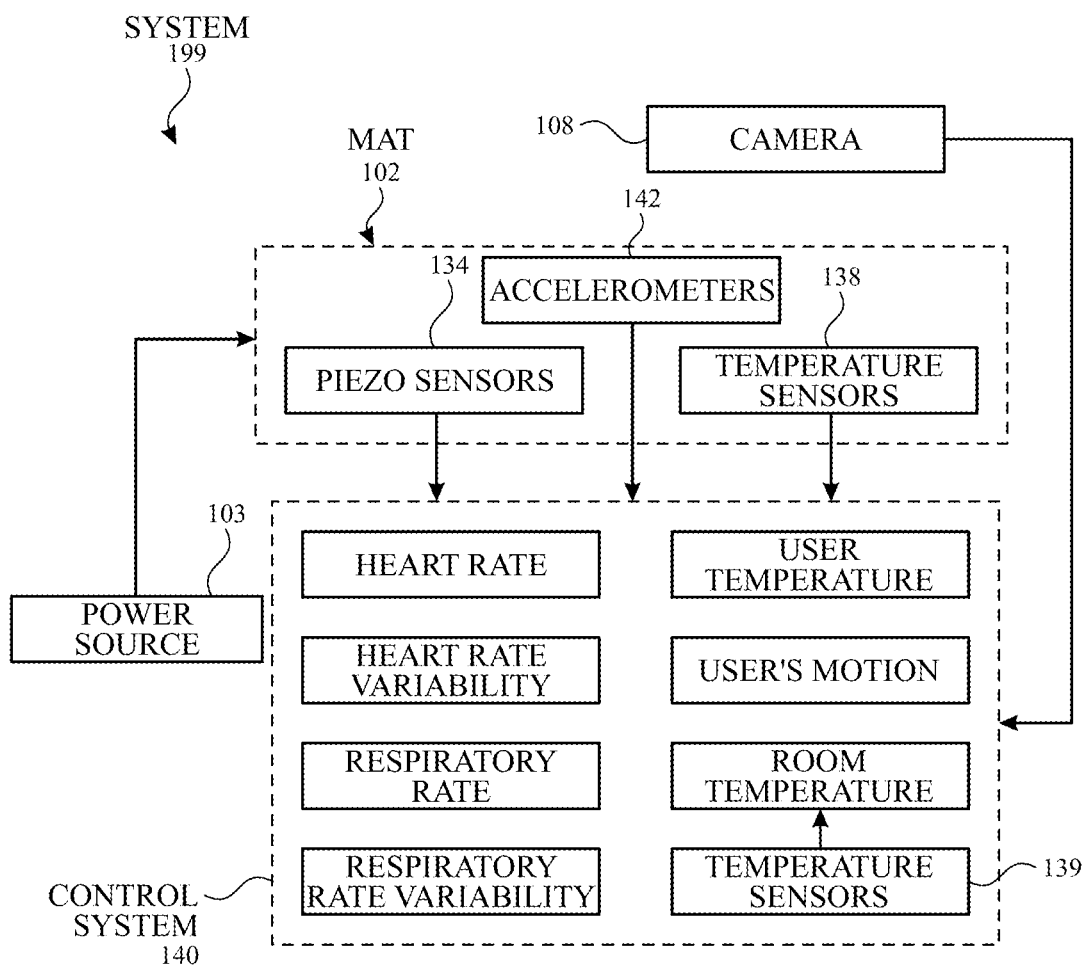
FIG. 1 illustrates an exemplary block diagram of a monitoring system according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

Disclosed herein are monitoring systems and sensors for physiological measurements. The sensors can be multi-element piezo sensors capable of generating multiple electrical signals, whereby the monitoring systems can receive the multiple electrical signals to analyze the user's vital signs along multiple regions of the user's body. In some examples, the piezo sensor can include one or more corrugations, such as peaks and valleys, to create localized regions with increased mechanical response (e.g., sensitivity) to force. The sensitivity and resolution of the piezo sensor can be enhanced by further locating electrode sections at the corrugations, where the electrode sections can be electrically isolated and independently operable from other electrode sections. Traces electrically connecting an electrode section to, e.g., an off-panel controller can be routed over and/or around other electrode sections by including an insulator to electrically insulate from the other electrode sections or by using vias to route through one or more layers. The multi-element piezo sensor can include multiple piezo films and multiple pairs of electrodes (and/or electrode sections).

Examples of the disclosure also include piezo sensors having multiple piezo film elements, where the force (e.g., stress) can be concentrated onto the piezo film elements. Each piezo film element can be structurally and electrically isolated from other piezo film elements. Force concentration can be performed by configuring one or more intermediate layers to have a tapered profile, including one or more structures to transfer the force to the piezo film elements, configuring one or more intermediate layers to have regions of different force concentration, or a combination thereof. Examples of the disclosure further include piezo sensors configured for converting one type of force into another type of force by Poisson conversion.

FIG. 1 illustrates an exemplary block diagram of a monitoring system according to examples of the disclosure. System 199 can include mat 102, power source 103, camera 108, and control system 140. Mat 102 can be resting on, attached to, or in contact with a bed (not shown), for example. Although the discussion below is directed to a mat in contact with a bed, examples of the disclosure include other types of apparatuses configured to be in contact with one or more human users, one or more pets, or the like. That is, the mat can be in direct contact with the human(s)/pet(s), or the mat can be in contact with one or more intermediate layers, which directly contact the human(s)/pet(s). For example, mat 102 can be included in the user's clothing and can be configured for physiological measurements when the clothing is worn by the user. Mat 102 can be configured to cover all or a portion of a mattress, for example, that can be resting on, attached to, or supported by one or more frames of the bed. In some examples, mat 102 can be flexible. In some examples, mat 102 can be at least partially rigid. Mat 102 can include one or more of a sheet, blanket, duvet, pillow, pillowcase, or insert. Mat 102 can be a stand-alone unit that can be placed on a bed and can be incorporated into the fabric or textile used as part of a sleeping/resting arrangement.

Power source 103 can be configured to provide power to mat 102, control system 140, camera 108, or any combination thereof. In some examples, power source 103 can be coupled to a power outlet. In some examples, power source 103 can be coupled to a battery and a charging station or power supply. In some examples, power source 103 can be configured to receive power from a charging element, such as a magnetic puck. In some examples, the charging element can include an inductive coil, and power can be transferred to system 199 via an electromagnetic field.

System 199 can include camera 108 and control system 140. Camera 108 can be a video camera configured to perform one or more functionalities, including, but not limited to, determining the position of the user's body, determining the location of the user's body, determining the temperature of the user's body, and determining the temperature of the local ambient. The monitoring system can be configured to utilize the information from camera 108 in conjunction with the information from the one or more sensors (e.g., piezo sensors) for physiological measurements (e.g., heart rate measurements), analysis (e.g., sleep analysis), and feedback.

Control system 140 can be configured to control one or more parameters. For example, control system 140 can include temperature sensors 139, which can measure and provide information to the control system 140 about the temperature of the room that system 199 is located in. In some examples, control system 140 can be configured to communicate with mat 102 through wired (e.g., using a cable) or wireless communications. Control panel 140 can include a touch panel and/or a display and can be configured to interface with the user and/or a computer. For example, control panel 140 can display heart rate, heart rate variability, respiratory rate, respiratory rate variability, user's motion, and user's temperature. In some examples, control panel 140 can display analysis regarding the user's sleep and/or can provide suggestions to improve the user's sleep.

Mat 102 can include one or more sensors such as piezo sensors 134, temperature sensors 138, and accelerometers 142. The sensors can include one or more functionalities and configurations discussed below. Although FIG. 1 illustrates mat 102 as including three different types of sensors, examples of the disclosure can include a monitoring system that includes fewer or more sensors and/or different types of sensors (e.g., electrodes configured for impedance cardiography (ICG), electrocardiogram (ECG), and/or ballistocardiograph (BCG) measurements).

While control system 140 can be included in system 199, examples of the disclosure can include any arrangement where control system 140 is separate and distinct from system 199. System 199 can communicate information (e.g., physiological measurements, raw data from the piezo sensors, etc.) to control system 140 through wired or wireless (e.g., local area network) communication means. In some examples, control system 140 can include a transceiver to receive information and a controller or processor to process the information for the analysis (e.g., to determine heart rate, heart rate variability, respiratory rate, and respiratory rate variability).

Figure 2A:
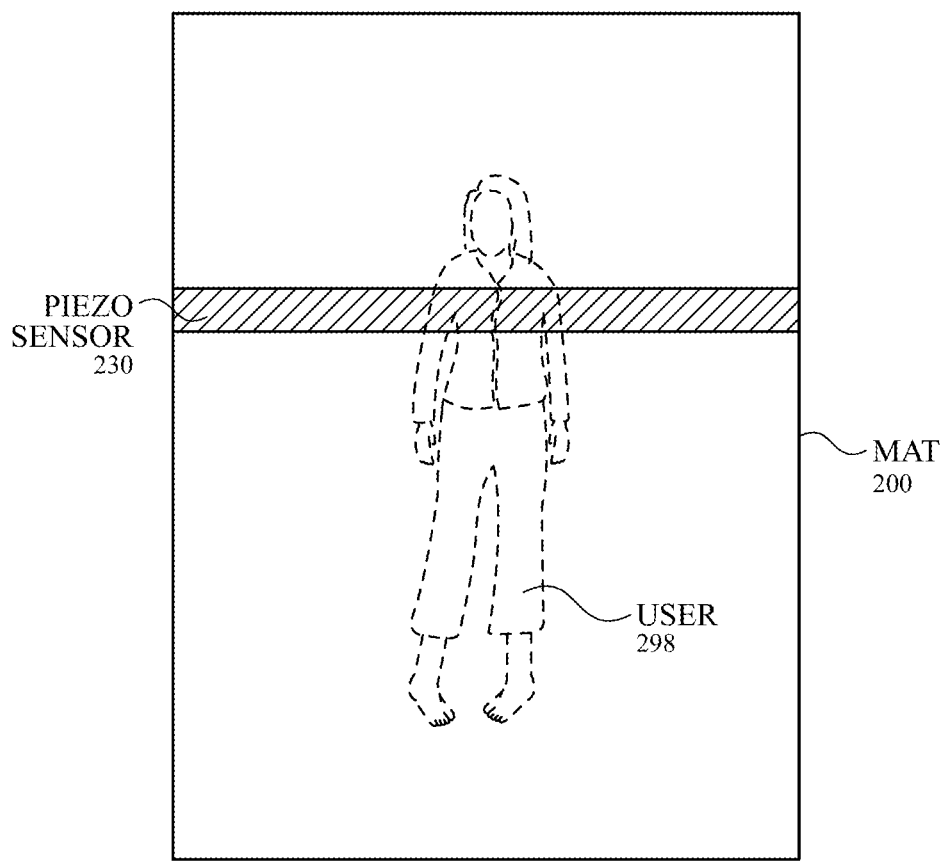
FIG. 2A illustrates a top view of an exemplary mat including a single element piezo sensor according to examples of the disclosure.

FIG. 2A illustrates a top view of an exemplary mat including a single element piezo sensor according to examples of the disclosure. Mat 200 can include piezo sensor 230. Piezo sensor 230 can include a polymer film (e.g., polyvinylidene fluoride (PVDF), copolymers with trifluoroethylene (P(VDF-TrFE)), poly-L-lactic acid (PLLA)) and an insulator located between a pair of electrodes, where the polymer film, insulator, and electrodes can cover the entire surface of the piezo sensor 230, thereby forming a single element piezo sensor. In some examples, the area of the polymer film, insulator, and electrodes can be the same.

Figure 2B:
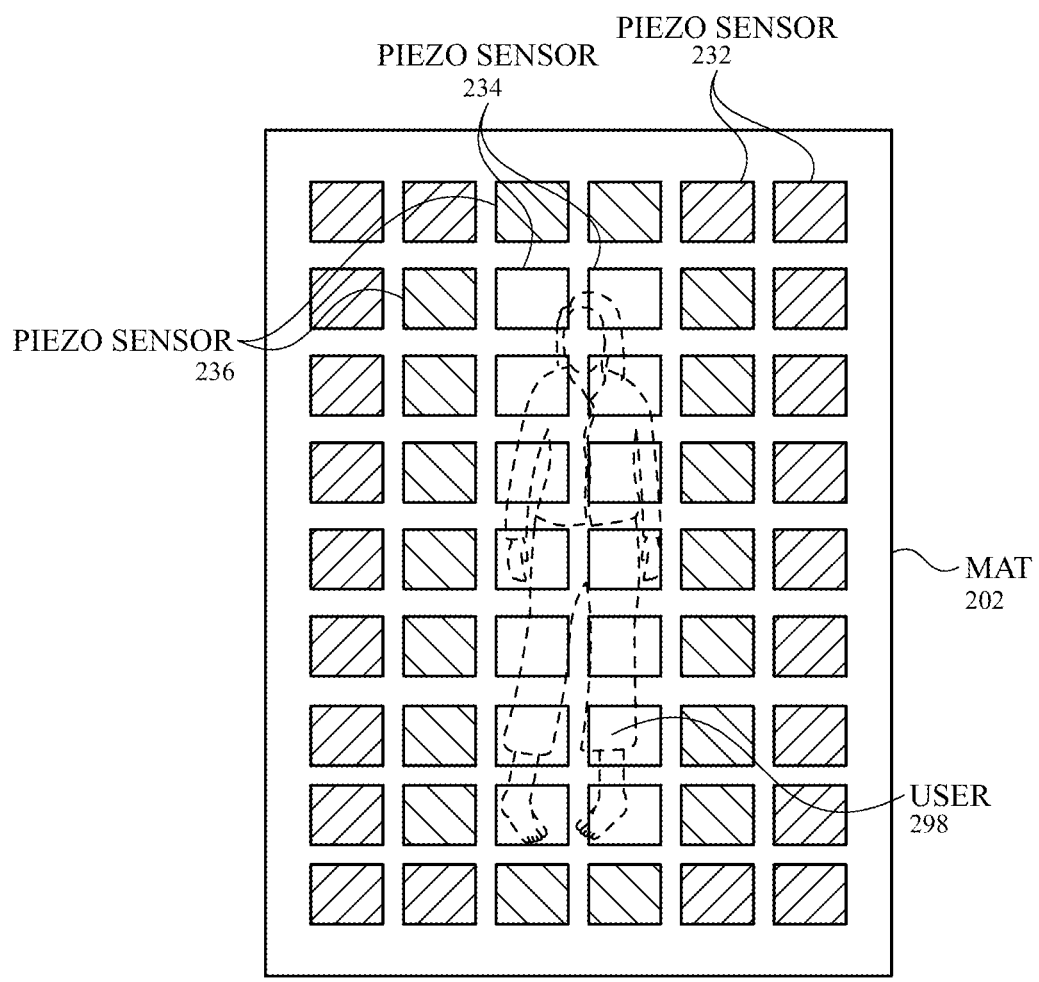
FIG. 2B illustrates a top view of an exemplary mat including multi-element piezo sensors according to examples of the disclosure.

The measurement accuracy and sensitivity can be enhanced by using multiple piezo sensors, which can be independently operable. FIG. 2B illustrates a top view of an exemplary mat including multi-element piezo sensors according to examples of the disclosure. Mat 202 can include a plurality of piezo sensors 232, piezo sensors 234, and piezo sensors 236. Piezo sensors 232, piezo sensors 234, and piezo sensors 236 can be multi-element piezo sensors, discussed in more detail below. In some examples, piezo sensors 232, piezo sensors 234, and piezo sensors 236 can be the same type of sensors. Mat 202 can be capable of discerning between sensors located directly under the body of user 298, sensors located in the immediate periphery of the body of user 298, and sensors located elsewhere. As illustrated in the figure, piezo sensors 234 can be located directly under the body of user 298. Piezo sensors 236 can be located in the immediate periphery (i.e., adjacent to the sensors, such as piezo sensors 234, located directly under the body of user 298). Piezo sensors 232 can be located elsewhere (e.g., in the periphery of mat 202). In some examples, one or more sensors can be located in both the immediate periphery of the body of user 298 and the periphery of mat 202. In some examples, the monitoring system can be configured to generate a two- or three-dimensional image representing the user's position, orientation, and/or body force.

By having the capability to discern between sensors located in different regions of mat 202, the monitoring system can correlate certain signals (from the piezo sensors) with certain regions of the user's body, thereby enhancing the accuracy of the measurement, analysis, and feedback to the user. For example, sensors (e.g., piezo sensors 236) located in the immediate periphery of the user's body can be more sensitive to gross motion of user 298 than sensors located directly under user 298. The monitoring system can correlate the signals from piezo sensors 234 with motion of the user's chest cavity, for example. On the other hand, motion detected by sensors (e.g., piezo sensors 232) located elsewhere (e.g., in the periphery of mat 202) may not be due to the motion of user 298. Instead, for example, the motion can be due to a second user, and the system can correlate the signals from piezo sensors 232 with the motion of the second user rather than mistakenly associating the signals to the first user (e.g., user 298). Additionally, the capability of discerning between sensors located in different regions can help the monitoring system differentiate between gross motion and fine body movements. For example, although a user's breathing can cause a motion artifact, the breathing motion can differ from gross motion (e.g., due to the user moving or stirring). The system can distinguish between motion due to the user breathing and motion due to the user moving.

Figure 2C:
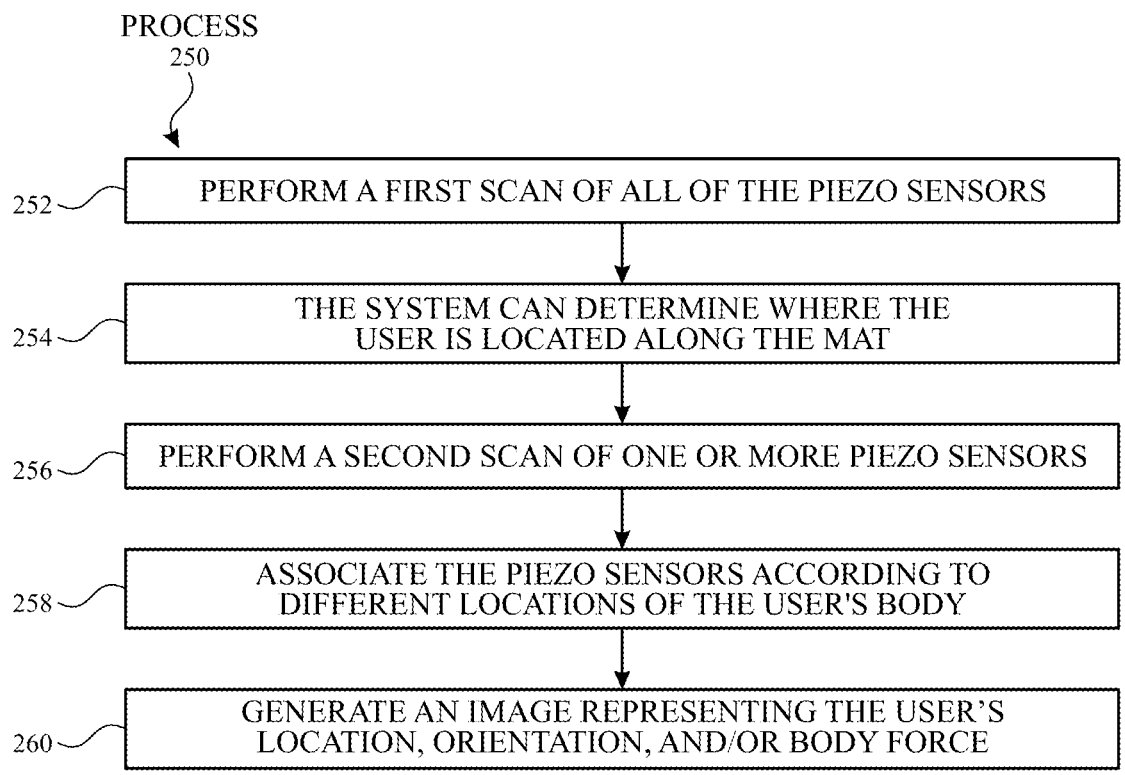
FIG. 2C illustrates an exemplary method for configuring the piezo sensors included in the mat according to examples of the disclosure.

In some examples, the monitoring system can be capable of determining and dynamically configuring which piezo sensors are associated with the position and orientation of the user's body. Additionally or alternatively, the monitoring system can be capable of dynamically changing the modality of a given piezo sensor. FIG. 2C illustrates an exemplary method for configuring piezo sensors included in a mat according to examples of the disclosure. The monitoring system can perform a first scan of all of the piezo sensors (step 252 of process 250). The first scan can be, for example, a high-level scan to determine roughly where the user is located along the mat (step 254 of process 250). The monitoring system can perform a second scan of one or more piezo sensors, such as piezo sensors potentially located in the immediate periphery of the user's body (step 256 of process 250). The piezo sensors that are potentially located in the immediate periphery of the user's body can be, for example, those piezo sensors measuring a force, while also located adjacent to piezo sensors that do not measure force. In some examples, the granularity of the second scan can be greater than the granularity of the first scan. In some examples, the second scan can include measuring a fewer number of piezo sensors than the first scan. The monitoring system can associate the piezo sensors according to the different locations of the user's body (step 258 of process 250). Optionally, the monitoring system can perform subsequent scans with increased granularity at one or more regions of the mat. The monitoring system can generate an image representing the user's location, orientation, and/or body force (step 260 of process 250).

The piezo sensors included in the monitoring system can be any type of piezo sensors including, but not limited to, piezoelectric or piezoresistive sensors. The piezo sensors can include piezo films made of, for example, PVDF, P(VDF-TrFE), and/or PLLA. The piezo sensors can be arranged to contact the user's body and can be configured to detect mechanical distortions at the external surface of the piezo sensor (e.g., interface of the mat and the user's body). Movement of the user's body (e.g., chest cavity) due to blood flow to the heart and/or respiration in the lungs can cause mechanical distortions or deformations at the external surface of the piezo sensor. The mechanical distortions or deformations can propagate to the piezo sensors. The piezo sensors can detect one or more changes in the mechanical properties (e.g., amount of pull, compression, twisting, etc.) of the piezo sensors and can generate one or more electrical signals indicative of the one or more changes in mechanical properties. The system can use the one or more electrical signals to determine the user's physiological information (e.g., heart rate, heart rate variability, respiratory rate, and respiratory rate variability).

Figure 3:
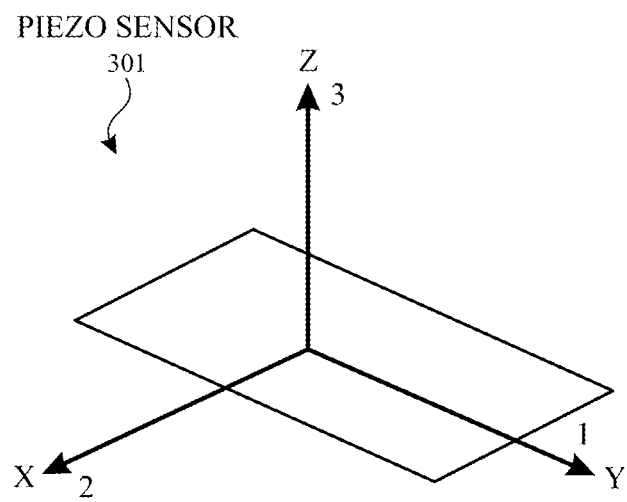
FIG. 3 illustrates an exemplary piezo sensor including a piezo film according to examples of the disclosure.

In some examples, the piezo sensor can include planar layers. FIG. 3 illustrates an exemplary piezo sensor including a piezo film according to examples of the disclosure. Piezo sensor 301 can be capable of being subject to mechanical forces. The monitoring system can be configured to apply an electrical poling field on the piezo film to sensitize the film to particular mechanical distortions (e.g., compression, bending, etc.). For example, a piezo film having a d33 mode can have an applied field strength and an applied force (or induced strain) both in the direction of the z-axis. The electrical signal can be indicative of the compression applied along the z-axis direction. Alternatively, a piezo film having a d31 mode can have an applied field strength in the direction of z-axis, along with an applied force (or induced strain) in the direction of the y-axis. The electrical signal can be indicative of the in-plane stretching along the y-axis. In some examples, piezo sensor 301 stackup can include a polymer film (e.g., PVDF or PLLA) and an insulator located between two electrodes, where the layers of the stackup can cover the entire surface of the piezo sensor 301 (e.g., piezo sensor 230 or piezo sensor 232).

Examples of the disclosure can include adjusting the dimension(s) of the piezo film to increase signal coupling. In some instances, the area (e.g., thickness, width, and/or length) of the piezo film can be increased, thereby increasing the coupling and/or response of the piezo film to the applied force. For example, the width of the piezo film can be increased (e.g., the width of piezo sensor 230 illustrated in FIG. 2A can be increased to 50% or greater than the width of mat 200). Due to the increased width, the piezo film can experience a higher amount of stretch in response to an applied force from the user's body. Increasing the area of the piezo film can also decrease inaccuracies and/or errors. For example, if the piezo sensor is not located directly under the user's heart, the heart rate and heart rate variability measurements may be inaccurate. Changing the dimensions of the piezo film can allow one or more piezo sensors to be located directly under certain body parts of the user. Moreover, the increased area can give the monitoring system the capability of selectively choosing which one or more piezo sensors to activate or include in the analysis, e.g., for enhanced signal-to-noise ratio (SNR) and/or signal quality.

In some instances, one or more dimensions of the piezo film can be decreased to lessen the degree of measuring movements unrelated to the desired measurements (e.g., heart rate, heart rate variability, pulse rate, and pulse rate variability). In some examples, one or more dimensions can be decreased to lessen the likelihood of measuring unwanted mechanical modalities (e.g., stretching, bending, etc.); alternatively, the one or more dimensions can be increased to capture a large number of mechanical modalities.

In some examples, the piezo sensor can include one or more corrugations. FIG. 4A illustrates a cross-sectional view of an exemplary piezo sensor including corrugations according to examples of the disclosure. Piezo sensor 401 can include a piezo film 411 having corrugations such as peaks 410 and valleys 412. Other corrugations can include, but are not limited to, folds, creases, and bends. The corrugations can create localized regions with increased mechanical response (e.g., sensitivity) to force 420. Piezo sensor 401 can further include a plurality of sections 414; each section can spatially separate adjacent corrugations (e.g., a section 414 can be located between a peak 410 and a valley 412). In some instances, peaks 410 (and/or valley 412) can be more sensitive to force 420 than sections 414. Electrical response to, for example, force 420 can also dependent on the relative stiffness of the various layers including stiffness of the electrodes. The stiffness can also be designed to enhance or mitigate electrical response.

For a given peak 410 and/or valley 412, force 420 can create a change in the angle of the corrugation with the corresponding induced piezoelectric signal, which can lead to a different response than force applied to a non-corrugated piezo film (e.g., piezo sensor 301). The changes in angles of some or all of the corrugations can be used to create a three-dimensional image of the movement of the user's body. In some examples, the piezo sensor 401 can include a piezo film 411 located between electrodes 413. Piezo film 411 can undergo mechanical distortions or deformations (from force 420) and can generate one or more electrical signals indicative of the changes in mechanical properties. Electrodes 413 can propagate the electrical signal(s) to a controller for processing and analysis. In some examples, electrodes 413 can each be a single electrode configured to couple to multiple (e.g., all) corrugations.

Figure 4B:
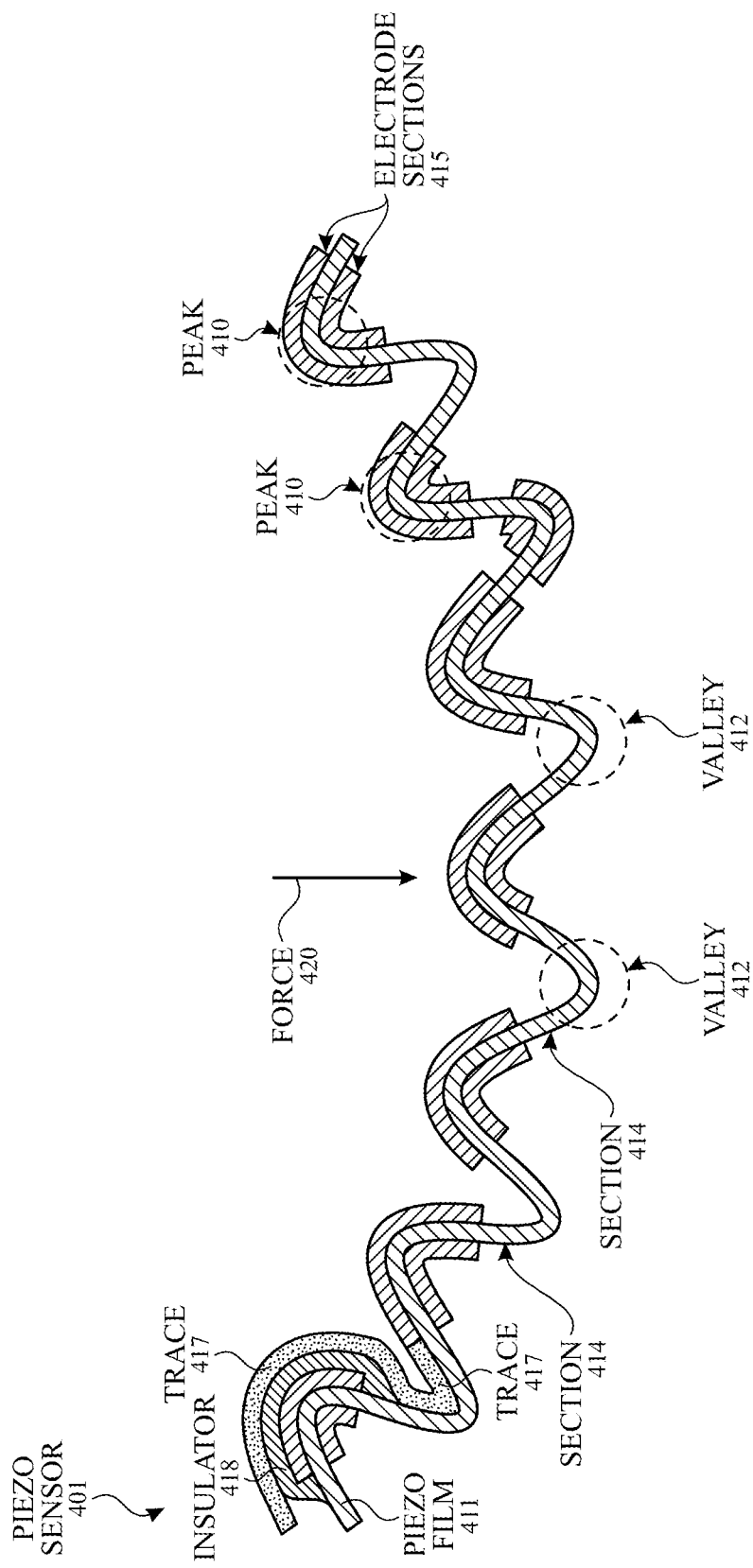
FIG. 4B illustrates a cross-sectional view of an exemplary piezo sensor including corrugations coupled to electrode sections according to examples of the disclosure.

In some examples, the electrodes located at the corrugations can be isolated electrodes sections, as illustrated in FIG. 4B. Each electrode section 415 can be electrically isolated and independently operable from other electrode sections 415. With electrode sections 415 located on the corrugations, the charge created by piezo film 411 (and measured by the corresponding electrode sections 415) can be due to mechanical forces located at the corrugations. In some instances, the charge at each corrugation can exclude mechanical forces detected at sections 414 (or any other regions less sensitive to mechanical force). The piezo film and electrodes located on the corrugations can enhance the sensitivity and resolution of piezo sensor 401. Mechanical (e.g., stiffness, relative size, etc.) differences in the electrode sections, for example, in electrode section 415 can also be designed to enhance or mitigate electrical response by affecting the transformation of deformation stress from the applied forces into material strain.

In some examples, each electrode section 415 can be routed using a trace 417. Each trace 417 can be disposed, but electrically isolated from (e.g., by including an insulator 418 adjacent to trace 417) one or more of the other electrode sections 415. For example, each pair of electrode sections can be electrically coupled to a corrugation separate from other pairs of electrode sections. An insulator 418 can be located between at least one electrode section corresponding to a first pair and another electrode section corresponding to a second pair. Alternatively or additionally, the traces can be routed around the other electrode sections 415, but on the same layer, for example. Although FIG. 4B illustrates one trace 417, one skilled in the art would understand that other traces 417 can be included and coupled to other electrode sections; one trace 417 is illustrated for clarity purposes. Electrical response to, for example, force 420 can also depend on the relative mechanical (e.g., stiffness) properties of the various traces, where the mechanical properties of the traces can be designed to enhance or mitigate electrical response.

In some examples, a voltage can be generated across each electrode section 415, and electrical signals from the electrode sections 415 can be aggregated (e.g., added together) and/or amplified. In some instances, the same force 420 can cause mechanical deformations of peaks 410 to be different from the mechanical deformations of valleys 412. As a result, the electrical signals from the peaks 410 can cancel (or reduce) the electrical signals from the valleys 412 if the electrical signals are merely added together.

Figure 4C:
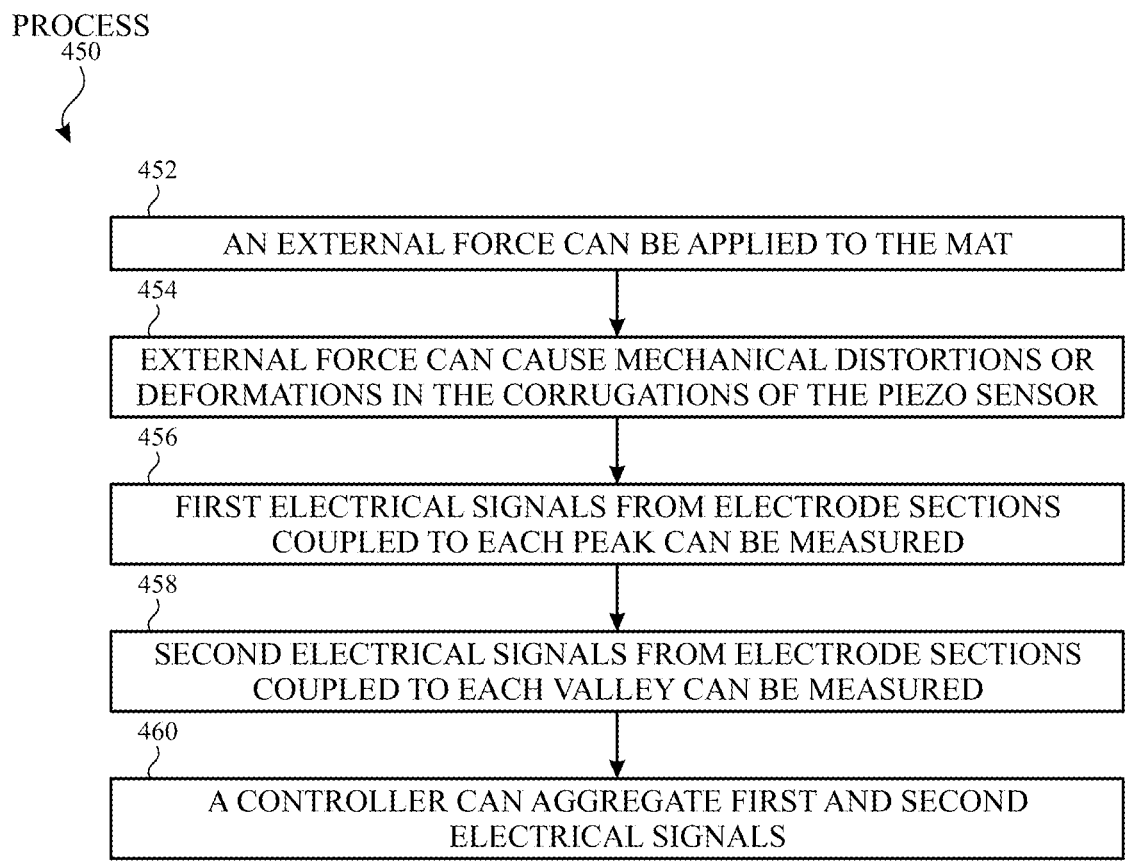
FIG. 4C illustrates an exemplary method for operating a corrugated piezo sensor including electrically isolated electrode sections according to examples of the disclosure.

To avoid cancellation (or unwanted reduction) of the electrical signals, the electrode sections 415 associated with peaks 410 can be subsampled with one polarity (or phase), and electrode sections 415 associated with valleys 412 can be subsampled with an opposite polarity (or phase). FIG. 4C illustrates an exemplary method for operating a corrugated piezo sensor including electrically isolated electrode sections according to examples of the disclosure. An external force can be applied to the mat (step 452 of process 450). The external force can cause mechanical distortions or deformations to the corrugations of the piezo sensor (step 454 of process 450). First electrical signals from electrode sections coupled to each peak of the corrugated piezo sensor can be measured (step 456 of process 450). Second electrical signals from electrode sections coupled to each valley can be measured (step 458 of process 450). In some examples, valleys can be measured before peaks are measured. In some examples, some peaks can be measured, followed by some valleys being measured, followed by some peaks being measured, etc. A controller can aggregate the electrical signals (step 460 of process 450) (e.g., the electrical signals can have different polarities or phases depending on the structure of the corrugation), which can lead to an enhanced overall electrical signal.

Figure 4D:
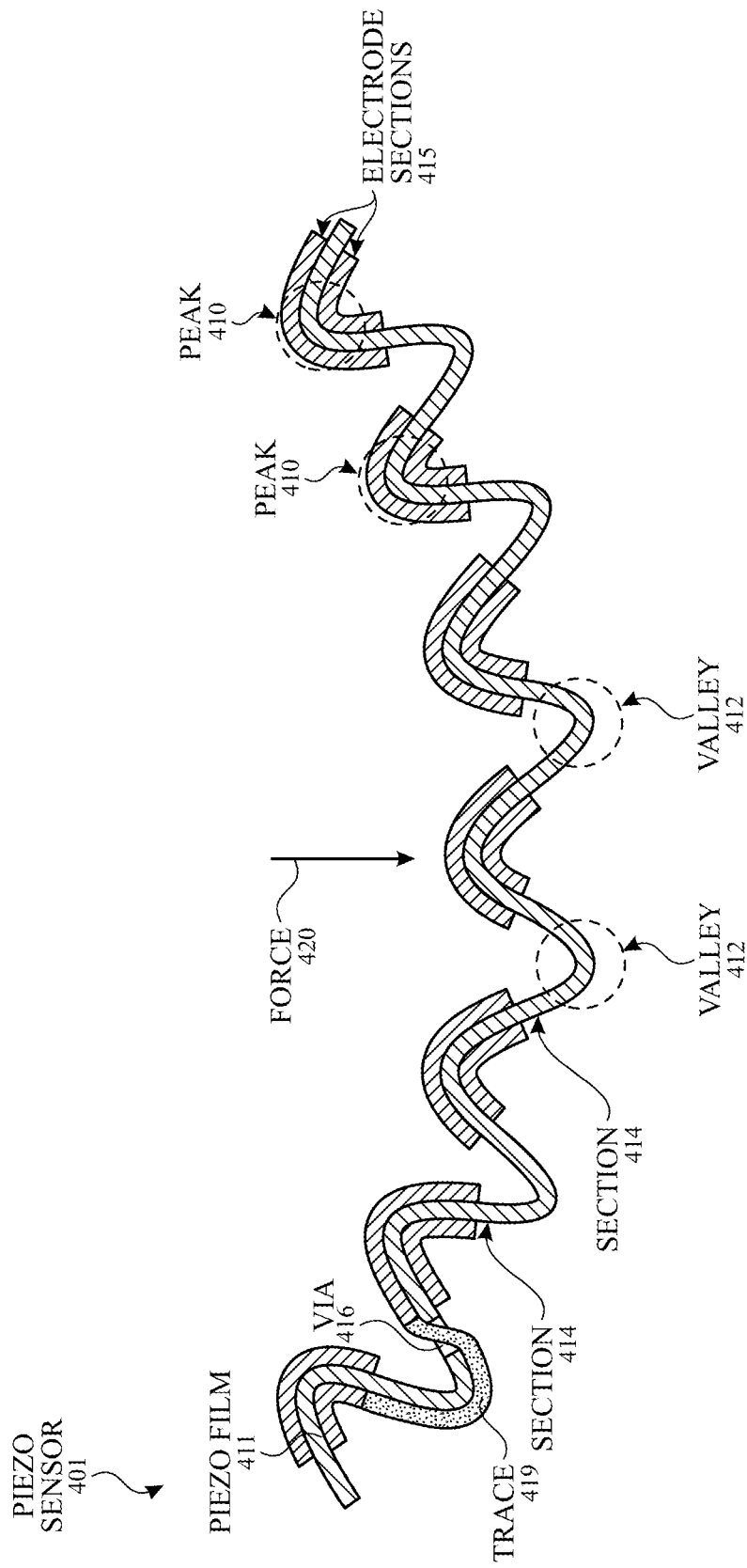
FIG. 4D illustrates a cross-sectional view of an exemplary piezo sensor including corrugations and electrically coupled electrode sections according to examples of the disclosure.

An alternative for avoiding or reducing cancellation of the electrical signals of the electrode sections can be to electrically couple some of the electrode sections together, as illustrated in FIG. 4D. For example, trace 419 can couple an electrode section 415 to a peak 410 and can couple an electrode section 415 to a valley 412. In some examples, one or more vias 416 can be used to route trace 419 from the one electrode section 415 located on one layer through the piezo film 411 to another electrode section 415 located on another layer. In some examples, one or more insulators (not shown) can be included to allow traces 417 and/or electrode sections 415 to cross over without electrically coupling.

Figure 5A:
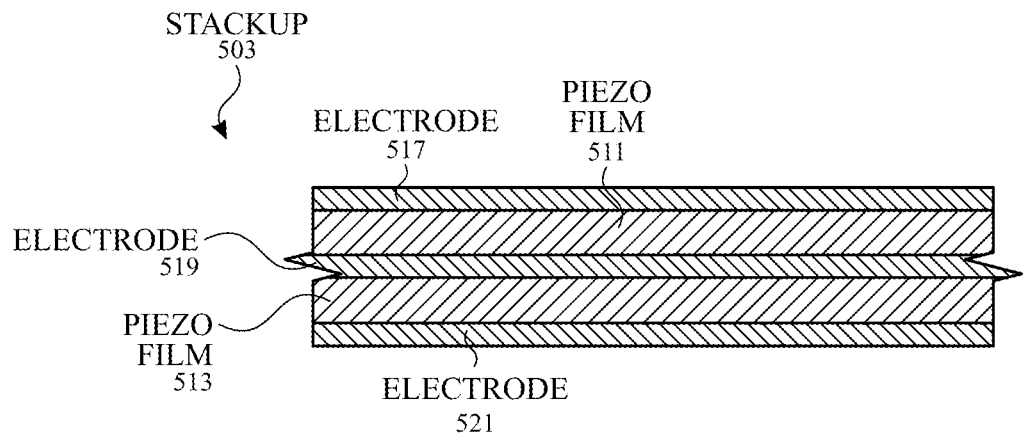
FIG. 5A illustrates a cross-sectional view of an exemplary piezo sensor including multiple layers according to examples of the disclosure.

Examples of the disclosure can include piezo sensors including multiple layers, such as illustrated in FIG. 5A. Stackup 503 can include electrode 517, electrode 519, and electrode 521 interleaved with piezo film 511 and piezo film 513. Electrode 517, electrode 519, and electrode 521 can each be single electrodes having the same area as the piezo films. In some examples, electrode 517 and electrode 519 can electrically couple to piezo film 511. In some examples, electrodes 519 and electrode 521 can electrically couple to piezo film 513. Examples of the disclosure can include corrugations (not shown). Electrical response to the applied force can also depend on the relative mechanical (e.g., stiffness) properties of the various traces, where the mechanical properties of the traces can be designed to enhance or mitigate electrical response.

Figure 5B:
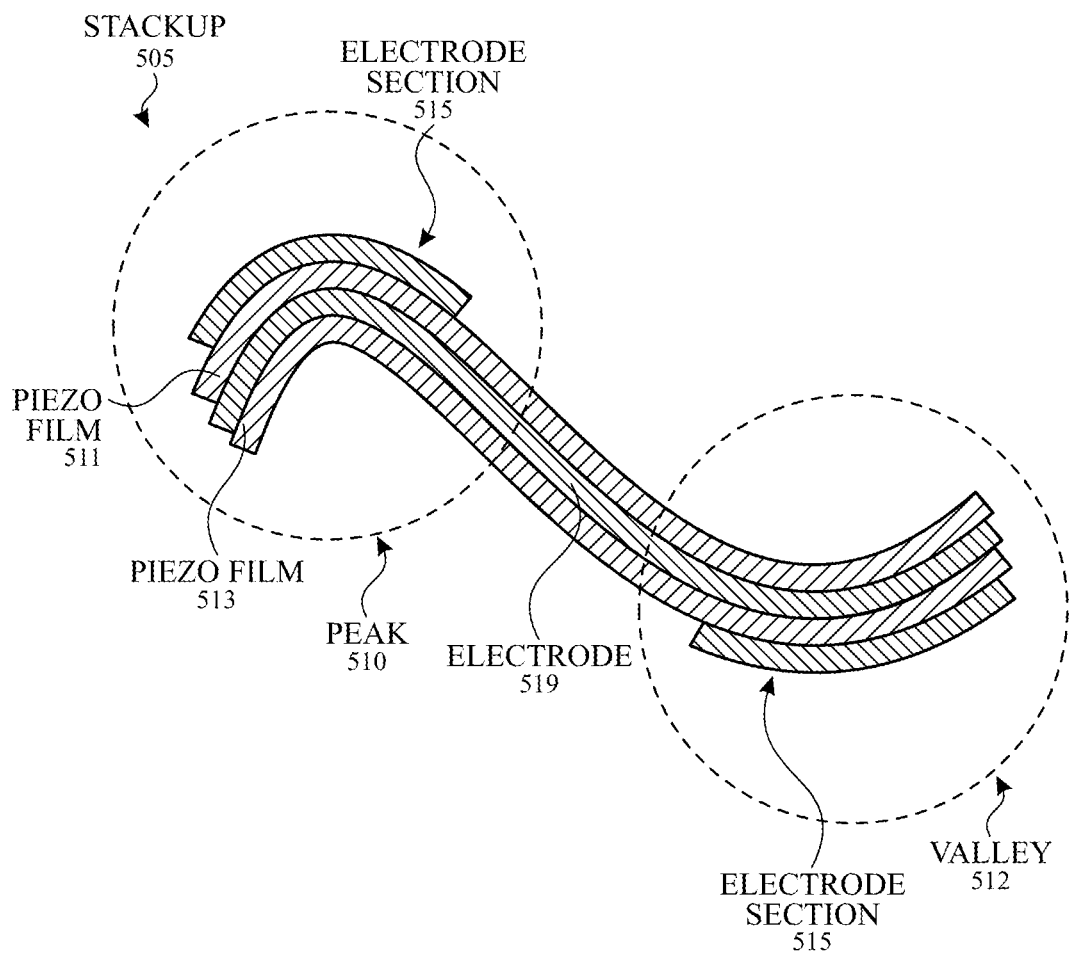
FIG. 5B illustrates a cross-sectional view of an exemplary piezo sensor including a single electrode located across corrugations according to examples of the disclosure.

In some examples, one or more electrodes can include electrode sections. For example, as illustrated in FIG. 5B, stackup 505 can include a single electrode 519 (e.g., having the same area as piezo film 511 and piezo film 513) that can be located in both peak(s) 510 and valley(s) 512. Stackup 505 can further include electrode sections 515, where each corrugation can include an electrode section 515. For example, at peak 510, electrode section 515 and electrode 519 can electrically couple to piezo film 511. At valley 512, electrode section 515 and electrode 519 can electrically couple to piezo film 513. Electrical response to the applied forces on the electrode sections can also depend on the relative mechanical (e.g., stiffness) properties of the electrode sections, where the mechanical properties of the traces can be designed to enhance or mitigate electrical response.

In some examples, electrode sections 515 can be located on the same side (e.g., outer side) of the corrugation (not shown). For example, at peak 510, an electrode section 515 can be located on the top of peak 510. At valley 512, an electrode section 515 can be located on the bottom of valley 512. In some examples, each corrugation can include multiple (e.g., two) electrode sections 515. For example, each corrugation can include an electrode section located on the top and an electrode section located on the bottom of the corrugation, in addition to electrode 519. The piezo electric sensor can be configured with multiple electrodes, thereby increasing the number of electrical signals. The electrical signals can be associated with different orthogonal layers to create a matrix of information, for example, associated with the user.

Figure 5C:
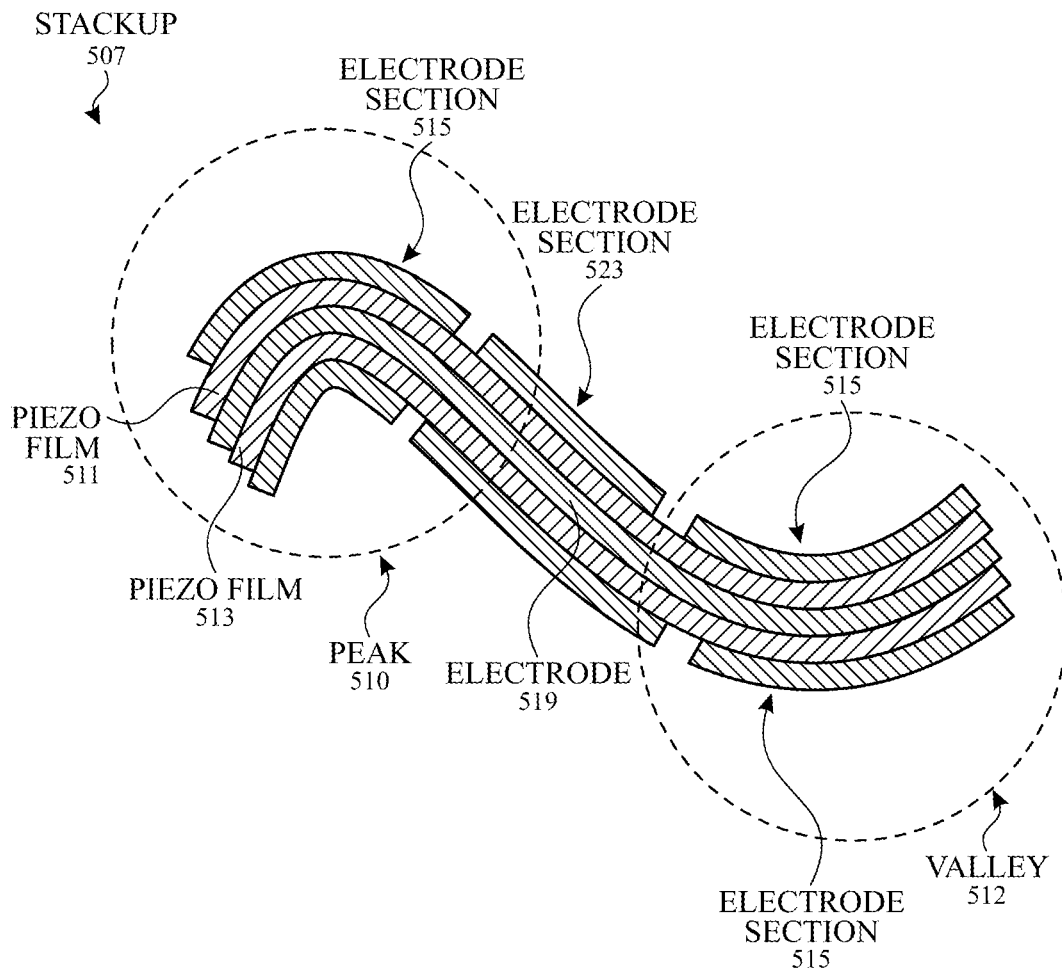
FIG. 5C illustrates a cross-sectional view of an exemplary piezo sensor including an electrode section located between corrugations according to examples of the disclosure.

Although the non-corrugated sections (located between corrugations) may have lower mechanical response (e.g., sensitivity to mechanical force) compared to the corrugations, the non-corrugated sections can still measure mechanical force, albeit possibly a different type and/or magnitude of mechanical force. In some examples, an electrode section 523 can be located at the non-corrugated sections in between corrugations, as illustrated in FIG. 5C. In some examples, electrode sections 515 and electrode sections 523 can each be individually routed and independently operable. In some examples, two or more electrode sections 515 can be electrically coupled together, and/or two or more electrode sections 523 can be electrically coupled together. Although FIG. 5C illustrates electrode sections 523 located on both sides of the stackup 507, examples of the disclosure can include an electrode section located on one side (e.g., on top) of stackup 507, without being limited to the same side for each non-corrugated section.

Figure 6A:
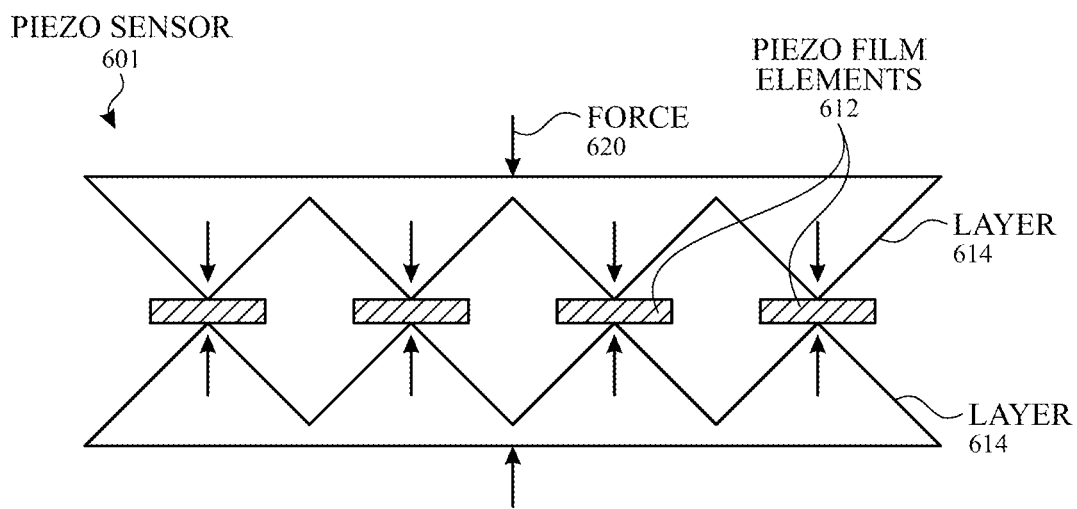
FIG. 6A illustrates a cross-sectional view of an exemplary piezo sensor including multiple piezo film elements, the piezo sensor configured for force concentration according to examples of the disclosure.

Examples of the disclosure can further include piezo sensors having multiple piezo film elements, where the force (e.g., stress) can be concentrated onto the piezo film elements. FIG. 6A illustrates an exemplary piezo sensor including multiple piezo film elements according to examples of the disclosure. Piezo sensor 601 can include piezo film elements 612, where each piezo film element 612 can be structurally and electrically isolated from the other piezo film elements 612. In some examples, piezo film elements 612 can be coupled to electrodes (not shown), which can generate independent electrical signals and/or can be independently operable. The piezo film elements 612 can include one or more intermediate layers, such as layer 614, configured to transfer force 620 to the piezo film elements 612. That is, layer 614 can concentrate compressive (i.e., transverse) forces at the external surface of the piezo sensor (e.g., interface of the mat (or the bed) and user's body) to piezo film elements 612. In some examples, layer 614 can be tapered, thereby allowing force 620 applied across the top of the piezo sensor 601 to concentrate at piezo film elements 612 (e.g., force applied across a larger region can be concentrated to multiple, smaller regions). Layer 614 can be configured with a larger volume of material located closer to the external surface of the piezo sensor 601 (e.g., the surface directly contacting the mat, bed, and/or user) than the piezo film elements 612. Piezo film elements 612 can include one or more functions and/or structure (e.g., corrugations), as discussed above. Although FIG. 6A illustrates two layers 614 surrounding piezo film elements 612, examples of the disclosure can include any number of layers 614, such as one layer 614. Examples of the disclosure further include electrodes and routing traces coupled to the piezo film elements 612, although not illustrated in the figure. The electrodes and routing traces can have one or more functions and/or structures as electrodes and routing traces described previously.

Figure 6B:
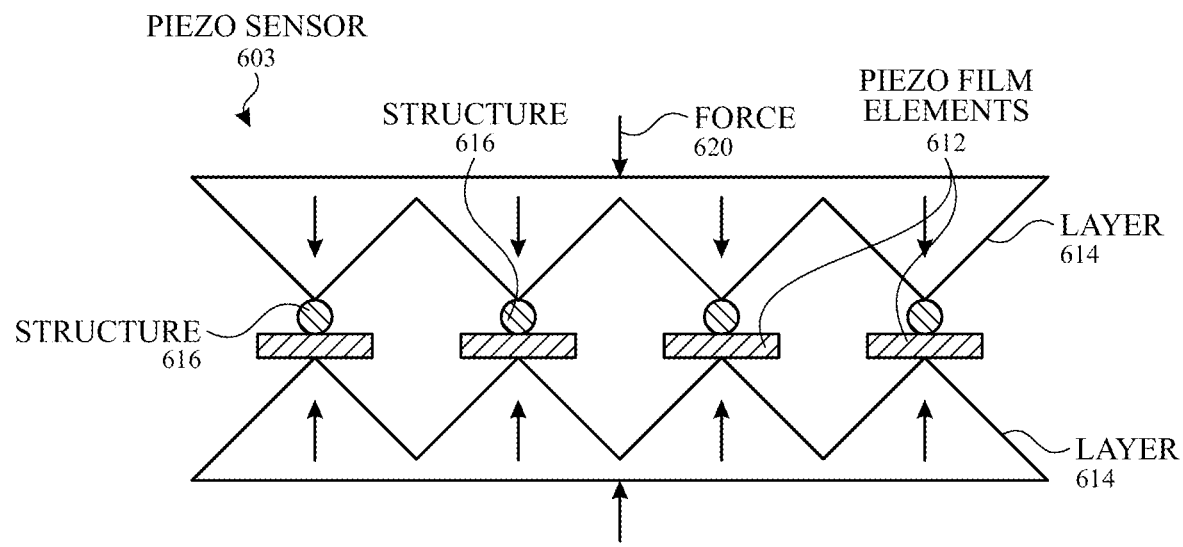
FIG. 6B illustrates a cross-sectional view of an exemplary piezo sensor including multiple piezo film elements and one or more structures, the piezo sensor configured for force concentration according to examples of the disclosure.

In some examples, as illustrated in FIG. 6B, piezo sensor 601 can include one or more structures 616 located between layer 614 and piezo film elements 612 to enhance the transfer of mechanical force 620 to the piezo film elements 612. By concentrating the force, the monitoring system can better capture mechanical deformations (e.g., local bending). Although FIG. 6B illustrates one or more structures 616 located on one side of piezo film elements 612, examples of the disclosure can include one or more structures located on multiple sides of piezo film elements 612.

Figure 6C:
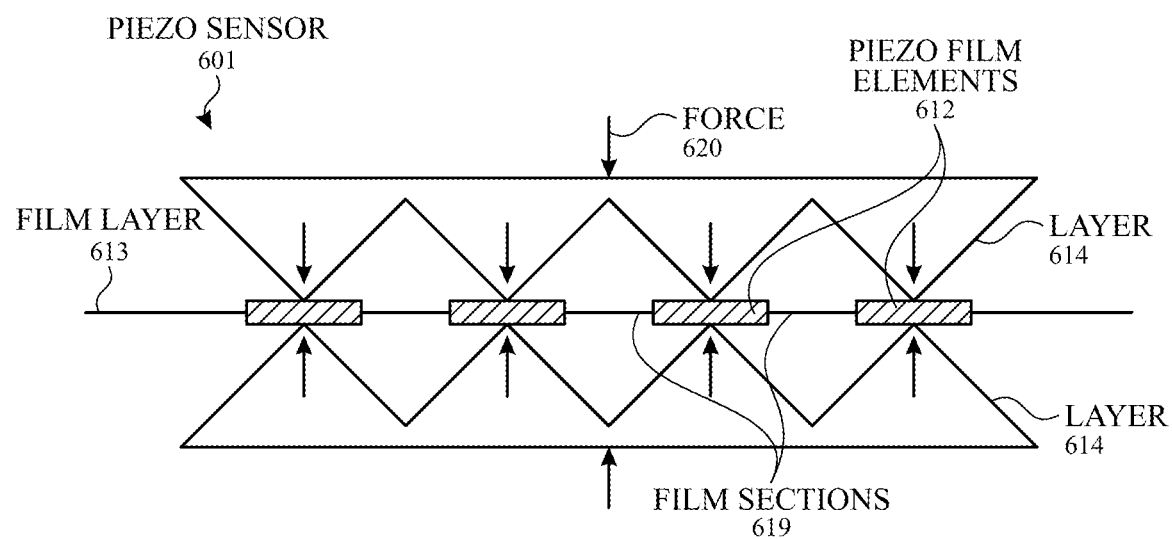
FIG. 6C illustrates a cross-sectional view of an exemplary piezo sensor including multiple piezo film elements connected by a film layer, the piezo sensor configured for force concentration according to examples of the disclosure.

Although the figures illustrate piezo film elements 612 as discrete elements, examples of the disclosure can include piezo film elements 612 structurally connected by a film layer, as illustrated in FIG. 6C. Each piezo film element 612 can be physically separated from other piezo film elements 612 by film sections 619. In some examples, the film sections can be responsive to mechanical forces applied to the film layer 613. The mechanical force experienced by the film sections 619 can propagate to one or more piezo film elements 612. In some instances, forces applied to discrete piezo film elements 612 not connected through a film layer can cause the discrete piezo film elements to move, but such movement may not be sensed by the monitoring system. Film layer 613 can help prevent any missed movements. In some examples, films sections 619 can have a different force concentration (e.g., mechanical strength, rigidity, and/or material density) than piezo film elements 612. In such a manner, film sections 619 can experience a different amount (e.g., less) of force 620 than piezo film elements 612. In some instances, film sections 619 can be less sensitive to force than piezo film elements 612.

Figure 6D:
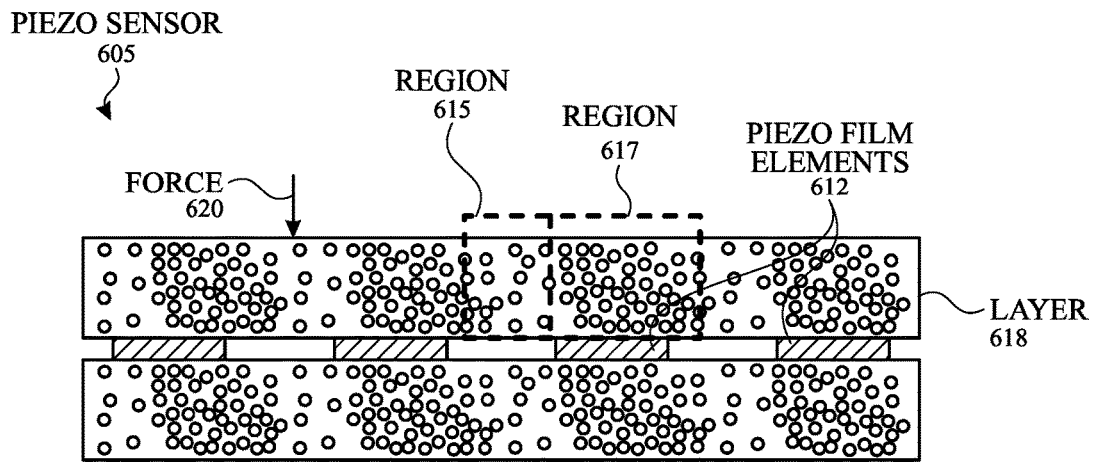
FIG. 6D illustrates an exemplary piezo sensor including intermediate layers having regions of differing force concentration according to examples of the disclosure.

In some examples, force concentration can be implemented by configuring the intermediate layer(s) to have regions of different force concentration (e.g., mechanical strength, rigidity and/or density). FIG. 6D illustrates an exemplary piezo sensor including an intermediate layer having regions of differing force concentration according to examples of the disclosure. Layer 618 can include multiple (e.g., two) regions such as region 615 and region 617 having different structural properties. For example, region 617 can include a higher density material than region 615. Layer 618 can be configured to transfer mechanical force 620 to the piezo film elements 612. The difference in density in region 617 relative to region 615 can cause region 617 to concentrate a greater amount of force from force 620 than region 615, and electrodes coupled to the piezo film elements 612 can generate electrical signals indicative of the force. In some examples, the dimensions (e.g., thickness) of the region 615 and region 617 can be the same.

Figure 6E:
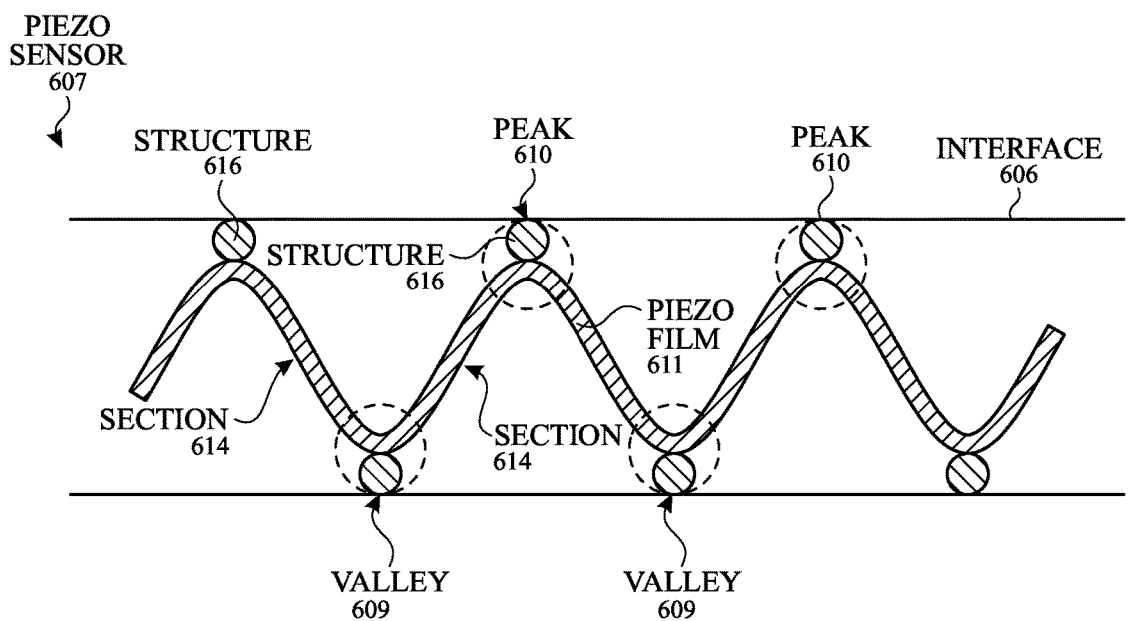
FIG. 6E illustrates an exemplary piezo sensor including a corrugated piezo film and one or more structures, the piezo sensor configured for force concentration according to examples of the disclosure.

Force concentration can also be implemented using a corrugated piezo film and one or more structures, as illustrated in FIG. 6E. Piezo sensor 607 can include a piezo film 611 having corrugations such as peaks 610 and valleys 609. Other corrugations can include, but are not limited to, folds, creases, and bends. The corrugations can create localized regions with increased sensitivity to mechanical force. Piezo sensor 607 can also include a plurality of non-corrugated sections 614, each non-corrugated section 614 spatially separating adjacent corrugations (e.g., a section 614 can be located between a peak 610 and a valley 609).

Piezo sensor 607 can further include one or more structures 616 located between the interface 606 (e.g., an external surface of piezo sensor 607) and piezo film 611. In some examples, interface 606 can include a planar layer(s) of material. For a given corrugation (e.g., peak 610 or valley 609), structures 616 can transfer force applied to interface 606 to piezo film 611, creating a change in the angle of the corrugation; which can lead to a different response than force applied to a non-corrugated piezo film (e.g., piezo sensor 301 illustrated in FIG. 3). The changes in angles of some or all of the corrugations can be used to create a three-dimensional image of the movement of the user's body. In some examples, the stackup of piezo sensor 607 can include electrodes (not shown) and routing traces (not shown) electrically coupled to piezo film 611 to measure and route the electrical signals from piezo film 611 to a controller. The electrodes and routing traces can have one or more functions and/or properties of electrodes and routing traces as discussed above.

Figure 6F:
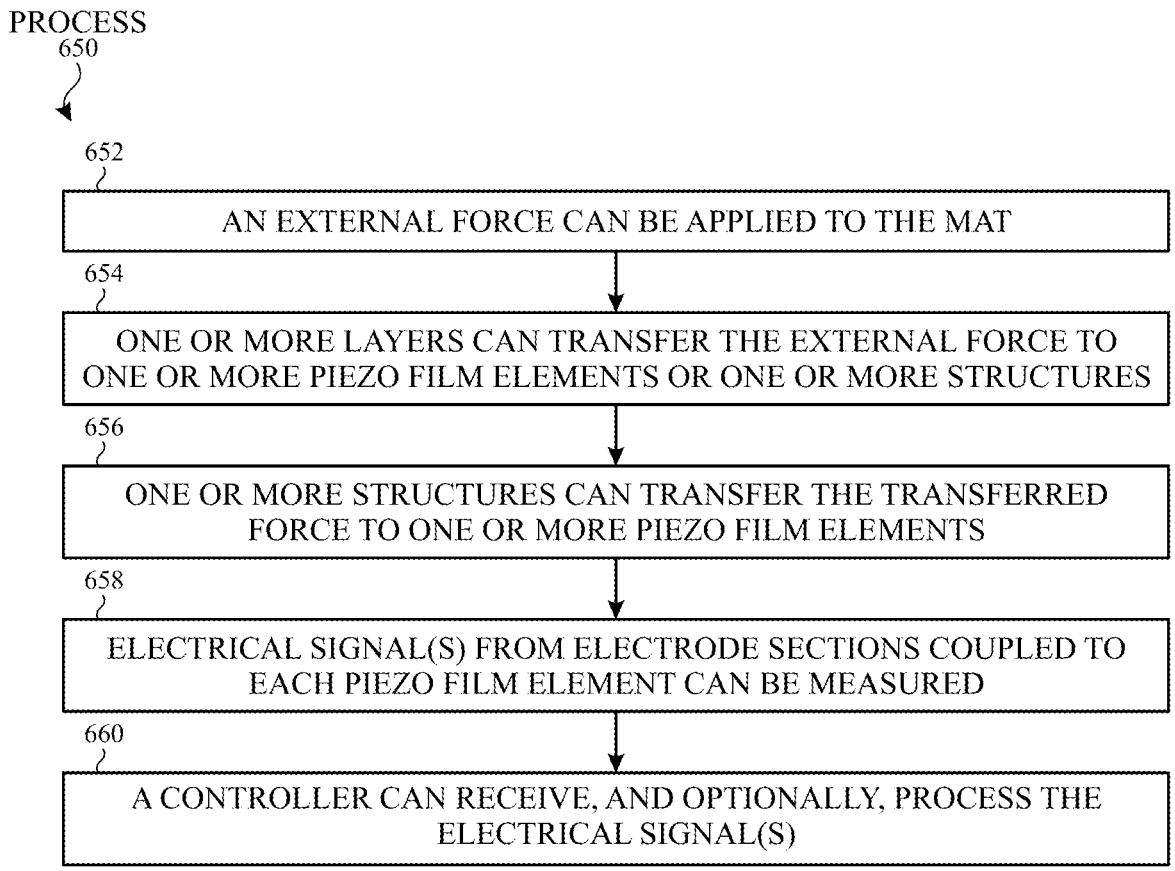
FIG. 6F illustrates an exemplary method for operating a piezo sensor including a plurality of piezo film elements according to examples of the disclosure.

FIG. 6F illustrates an exemplary method for operating a piezo sensor including a plurality of piezo film elements according to examples of the disclosure. An external force (e.g., force 620 illustrated in FIGS. 6A-6D) can be applied to the mat (step 652 of process 650). One or more layers (e.g., layer 614 illustrated in FIGS. 6A-6C, layer 618 illustrated in FIG. 6D, or a layer located at interface 606 of FIG. 6E) can transfer the external force to one or more piezo film elements (e.g., piezo film elements 612 illustrated in FIG. 6A-6D or piezo film 611 illustrated in FIG. 6E) or one or more structures (e.g., structures 616 illustrated in FIGS. 6B and 6E) (step 654 of process 650). Optionally, when applicable, the one or more structures can transfer the transferred force to one or more piezo film elements (step 656 of process 650). Electrical signal(s) from electrode sections coupled to each piezo film element can be measured (step 658 of process 650). A controller can receive, and optionally, process the electrical signal(s) (step 660 of process 650).

Figure 7:
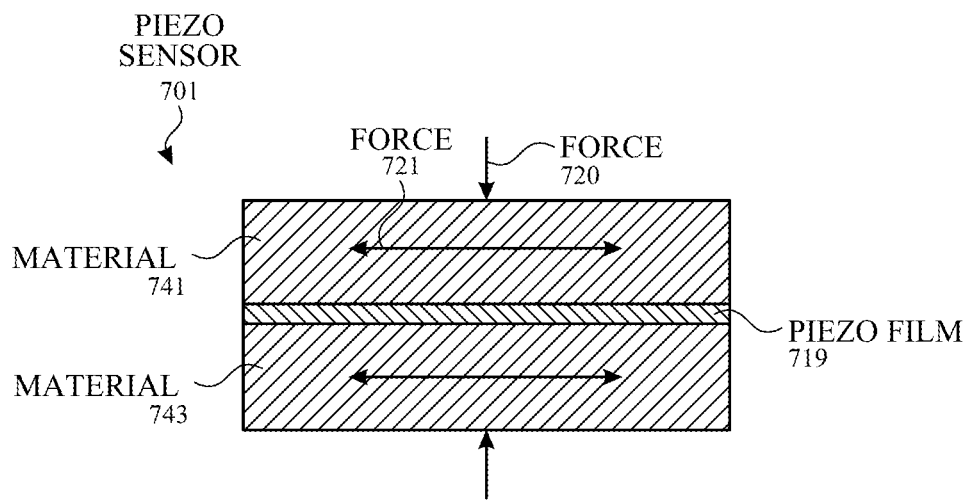
FIG. 7 illustrates an exemplary piezo sensor configured to convert forces by Poisson conversion according to examples of the disclosure.

Examples of the disclosure can further include piezo sensors configured for converting one type of force into another type of force by Poisson conversion. FIG. 7 illustrates an exemplary piezo sensor configured to convert forces by Poisson conversion according to examples of the disclosure. Piezo sensor 701 can include material 741 and material 743, where each material can convert an applied force into another type of force. That is, the piezo sensor 701 can convert the applied force 720 into a different mechanical mode. For example, the user's body can create a compressive force (i.e., transverse force) at the external surface of the piezo sensor 701 (e.g., interface of the mat and the user's body). Material 741 and material 743 can be, for example, a material with a high Poisson ratio. A material with a high Poisson ratio includes, but is not limited to, rubber. Material 741 and material 743 can experience the compressive force and can convert the compressive force into a lateral strain (i.e., longitudinal force). That is, compression of material 741, material 743, or both along one axis (e.g., z-axis) can result in expansion of the respective material along another axis (e.g., x-axis). Piezo sensor 701 can further include piezo film 719, which can be bonded to and located between material 741 and material 743. The lateral strain from material 741, material 743, or both can be transferred to piezo film 719, enhancing the d31 response (rather than a d33 response).

By including multiple elements in the piezo sensors, the monitoring system can analyze physiological information based on multiple mechanical modalities. For example, instead of measuring mere compressive forces due to the user's body weight, the piezo sensors can be capable of measuring both compressive and stretching forces. Furthermore, the monitoring system can include different types of piezo sensors and/or piezo sensors of the same type, but configured for multiple modalities. Referring back to FIG. 2B, for example, some piezo sensors 234 can be configured as a first type of piezo sensor (e.g., corrugated piezo sensors such as piezo sensor 401 illustrated in FIG. 4A) and other piezo sensors 234 can be configured as a second type of piezo sensor (e.g., force concentration piezo sensors such as piezo sensor 601 illustrated in FIG. 6A). As another example, some piezo sensors can be configured for a first mechanical modality (e.g., compression) and other piezo sensors can be configured for a second mechanical modality (e.g., bending). In some examples, the first type of piezo sensors and the second type of piezo sensors can be interleaved along the mat. Additionally or alternatively, the rows and/or columns of piezo sensors can be staggered. Examples of the disclosure can include the piezo sensors arranged in any configuration including, but not limited to, a configuration of rows and columns.

As discussed above, examples of the disclosure can include measuring a plurality of vital signs for one or more users. Additional information can be used to improve the delivery of measured information, analysis, or any other content that may be of interest to the users. In some examples, the measured information, analysis, or other content may include personal information that may uniquely identify the user or may be used to contact or locate the user. Such personal information can include geographic information, demographic information, telephone numbers, email addresses, mailing addresses, home addresses, or other identifying information. In some examples, the use of such personal information can be used to the benefit of the user. For example, the personal information can be used to deliver to the user the measured information, analysis, or other content. Use of personal information can include, but is not limited to, enabling timely and controlled delivery of the content.

The disclosure also contemplates that an entity that may be using (e.g., measuring, collecting, analyzing, disclosing, transferring, and/or storing) the personal information will comply with well-established privacy policies and/or privacy practices. These privacy policies and/or privacy practices can be generally recognized as meeting (or exceeding) industry or governmental requirements for private and secure personal information and should be implemented and consistently used. For example, personal information should be collected for legitimate and reasonable purposes and should not be shared (e.g., sold) outside of those purposes. Furthermore, collected personal information should occur only after receiving the informed consent of the user(s). To adhere to privacy policies and/or privacy practices, entities would take any steps necessary for safeguarding and securing outside access to the personal information. In some examples, entities can subject themselves to third party evaluation(s) to certify that the entities are adhering to the well-established, generally recognized privacy policies and/or privacy practices.

In some examples, the user(s) can selectively block or restrict access to and/or use of the personal information. The monitoring system can include one or more hardware components and/or one or more software applications to allow the user(s) to selectively block or restrict access to and/or use of the personal information. For example, the monitoring system can be configured to allow users to "opt in" or "opt out" of advertisement delivery services when collecting personal information during registration. In some examples, a user can select which information (e.g., home address) to withhold from the advertisement delivery services.

Although examples of the disclosure can include monitoring systems and methods for measuring vital signs with the use of the user's personal information, examples of the disclosure can also be capable of one or more functionalities and operation without the user's personal information. Lack of all or a portion of the personal information may not render the monitor systems and methods inoperable. In some examples, content can be selected and/or delivered to the user based on non-user specific personal (e.g., publicly available) information.

A multi-element piezo sensor is disclosed. In some examples, the multi-element piezo sensor comprises: a piezo film including a plurality of corrugations, each corrugation separated from another corrugation by a section, wherein each corrugation has a higher mechanical response to an external force than surrounding sections, the one or more corrugations configured to change an angle in response to the external force; a plurality of electrodes configured to electrically couple to the piezo film; and a plurality of routing traces configured to route one or more electrical signals from the plurality of electrodes to a controller. Additionally or alternatively, in some examples, at least one of the plurality of electrodes is a single electrode configured to electrically couple to multiple corrugations. Additionally or alternatively, in some examples, the plurality of electrodes are configured as a plurality of electrode sections, each pair of electrode sections electrically coupled to a corrugation separate from other pairs of electrode sections, each pair of electrode sections electrically isolated from other pairs of electrode sections. Additionally or alternatively, in some examples, the multi-element piezo sensor further comprises: a plurality of insulators, each insulator configured to electrically insulate pairs of electrode sections and located between at least two electrode sections corresponding to different pairs of electrode sections. Additionally or alternatively, in some examples, the piezo film includes at least one via, the plurality of corrugations includes at least one peak and at least one valley, and at least one routing trace electrically couples the at least one peak to the at least one valley and is routed through the at least one via. Additionally or alternatively, in some examples, the multi-element piezo sensor further comprises: a second piezo film; and a second electrode configured to electrically couple to the second piezo film, wherein at least one of the plurality of electrodes is further configured to electrically couple to the second piezo film. Additionally or alternatively, in some examples, the plurality of corrugations of the piezo film includes at least one peak and at least one valley, the multi-element piezo sensor further comprising: a second piezo film including a second plurality of corrugations, the second plurality of corrugations including: at least one peak corresponding to the at least one peak of the piezo film, and at least one valley corresponding to the at least one valley of the piezo film; and a second plurality of electrodes, wherein some of the second plurality of electrodes electrically couple to the piezo film, and others of the second plurality of electrodes electrically couple to the second piezo film. Additionally or alternatively, in some examples, the some of the second plurality of electrodes are located on a side of the piezo film, and the others of the second plurality of electrodes are located on an opposite side of the piezo film. Additionally or alternatively, in some examples, the multi-element piezo sensor further comprises: a plurality of electrode sections, each electrode section located between adjacent corrugations. Additionally or alternatively, in some examples, the multi-element piezo sensor further comprises: a plurality of structures configured to transfer force from an external surface of the multi-element piezo sensor to the plurality of corrugations, each structure located between the external surface and one of the plurality of corrugations.

A multi-element piezo sensor is disclosed. In some examples, the multi-element piezo sensor comprises: a plurality of piezo film elements, each piezo film element electrically isolated from the other piezo film elements; one or more layers, each layer configured to transfer force from an external surface of the multi-element piezo sensor to the plurality of piezo film elements; a plurality of electrodes configured to electrically couple to the plurality of piezo film elements; and a plurality of routing traces configured to route one or more electrical signals from the plurality of electrodes to a controller. Additionally or alternatively, in some examples, each layer includes a plurality of tapers, each taper having a larger volume of material closer to the external surface than the plurality of piezo film elements. Additionally or alternatively, in some examples, the multi-element piezo sensor further comprises: a plurality of structures configured to transfer force from the one or more layers to the plurality of piezo film elements, each structure located between one of the plurality of piezo film elements and the one or more layers. Additionally or alternatively, in some examples, the multi-element piezo sensor further comprises: a film layer including the plurality of piezo film elements and a plurality of film sections, each film section separating adjacent piezo film elements. Additionally or alternatively, in some examples, each film section has one or more different mechanical properties than each piezo film element. Additionally or alternatively, in some examples, each layer includes one or more first regions and one or more second regions, the one or more second regions configured to transfer a greater amount of force than the one or more first regions.

A multi-element piezo sensor is disclosed. In some examples, the multi-element piezo sensor comprises: two or more layers configured to respond to a first force modality applied to an external surface of the multi-element piezo sensor, the response including a Poisson conversion to a second force modality, different from the first force modality; one or more piezo films located between at least two of the two or more layers; a plurality of electrodes configured to electrically couple to the one or more piezo films; and a plurality of routing traces configured to route one or more electrical signals from the plurality of electrodes to a controller. Additionally or alternatively, in some examples, the first force modality is a compressive force, and the second force modality is a stretching force, and the one or more electrical signals includes information indicative of the stretching force.

A method for detecting an external force comprising: changing one or more mechanical properties of one or more corrugations of a piezo film in response to the external force; electrically coupling to the one or more corrugations of the piezo film; generating one or more electrical signals indicative of the change in the one or more mechanical properties; measuring the one or more electrical signals; and determining physiological information based on the measured one or more electrical signals. Additionally or alternatively, in some examples, measuring the one or more electrical signals includes: associating one or more first electrical signals with peaks of the one or more corrugations; measuring the one or more first electrical signals; associating one or more second electrical signals with valleys of the one or more corrugations; measuring the one or more second electrical signals; and aggregating the one or more first and the one or more second electrical signals.

Although examples have been fully described with reference to the accompanying drawings, it is to be noted that various changes and modifications will become apparent to those skilled in the art. Such changes and modifications are to be understood as being included within the scope of the various examples as defined by the appended claims.

What is claimed is:

1. A multi-element piezo sensor comprising:
a mat for placement on a sleeping surface and comprising:
a plurality of piezo film elements, each piezo film element electrically isolated from other piezo film elements;
one or more layers comprising:
an outer layer; and
an intermediate layer positioned between the outer layer the plurality of piezoelectric elements and comprising multiple structures, each structure of the multiple structures located between one of the plurality of piezo film elements and the outer layer and configured to concentrate a forced applied to the outer layer on a respective piezo film element of the multiple piezo film elements;
a plurality of electrodes configured to electrically couple to the plurality of piezo film elements; and
a plurality of routing traces configured to route one or more electrical signals from the plurality of electrodes to a controller, wherein the controller is configured to receive signals from the set of sensing elements and determine one or more physiological parameters of a user using the received signals.

2. The multi-element piezo sensor of claim 1, wherein each structure comprises a taper having a larger volume of material closer to the outer layer than the plurality of piezo film elements.

3. The multi-element piezo sensor of claim 1, further comprising:
a film layer including the plurality of piezo film elements and a plurality of film sections, each film section separating adjacent piezo film elements.

4. The multi-element piezo sensor of claim 3, wherein each film section has one or more different mechanical properties than each piezo film element.

5. The multi-element piezo sensor of claim 1, wherein the intermediate layer includes one or more first regions and one or more second regions, the one or more second regions configured to transfer a greater amount of force than the one or more first regions.

6. A multi-element piezo sensor comprising:
two or more layers configured to respond to a first force modality applied to an external surface of the multi-element piezo sensor,
one or more piezo films located between at least two of the two or more layers;
a plurality of electrodes configured to electrically couple to the one or more piezo films; and
a plurality of routing traces configured to route one or more electrical signals from the plurality of electrodes to a controller, wherein:
each layer of the two or more layers comprises multiple structures located between one of the one or more piezo films and an outer layer; and
each structures of the multiple structures is configured to concentrate a forced applied to the outer layer on a respective piezo film of the one or more piezo films.

7. A physiological sensing system comprising:
a mat for placement on a sleeping surface and comprising:
an outer layer;
a set of sensing elements arranged across the mat and configured to sense forces at different locations of the mat; and
an intermediate layer that transfers forces applied to an external surface of the mat to one or more sensing elements in the set of sensing elements, the intermediate layer comprising multiple structures each located between one of the one or more sensing elements and the outer layer and configured to concentrate a forced applied to the outer layer on a respective sensing element of the one or more sensing elements; and a processor configured to:
receive signals from the set of sensing elements; and
determine one or more physiological parameters of a user using the received signals.

8. The physiological sensing system of claim 7, wherein:
the set of sensing elements comprises a set of piezoelectric sensors;
the mat comprises multiple routing traces that are coupled to different piezoelectric sensors of the set of piezoelectric sensors; and
the multiple routing traces electrically couple a respective piezoelectric sensor to the processor.

9. The physiological sensing system of claim 8, wherein piezoelectric sensors of the set of piezoelectric sensors are arranged in a film layer that physically couples the piezoelectric sensors.

10. The physiological sensing system of claim 8, wherein each structure of the multiple structures comprises a respective taper.

11. The physiological sensing system of claim 7, wherein:
the intermediate layer is a first intermediate layer positioned on a first side of the set of sensing elements; and
the mat comprises a second intermediate layer positioned on a second side of the set of sensing elements, the second intermediate layer is configured to concentrate the forces applied to the area of the mat to the one or more sensing elements of the set of sensing elements.

12. The physiological sensing system of claim 11, wherein each of the first intermediate layer and the second intermediate layer includes structures that taper toward individual sensing elements of the set of sensing elements.

13. The physiological sensing system of claim 7, wherein the processor is configured to:
determine a location of a user with respect to the mat based on a first set of signals received from the set of sensing elements;
determine a subset of the set of sensing elements for measuring a physiological parameter based on the location of the user; and
determine the physiological parameter of the user using a second set of signals received from the subset of the set of sensing elements.

14. A physiological sensing mat comprising:
a first layer comprising an array of sensors each configured to sense a force at a respective location of the physiological sensing mat;
an array of electrodes comprising electrodes coupled to individual sensors of the array or sensors; and
a second layer coupled to the first layer and configured to transfer forces applied to an external surface of the physiological sensing mat to one or more sensors in the array of sensors, the second layer comprising multiple structures, each structure of the multiple structures positioned at a sensor of the array of sensors and configured to concentrate a forced applied to mat on a respective sensor of the array of sensors.

15. The physiological sensing mat of claim 14, wherein:
the second layer comprises a film having one or more first regions and one or more second regions; and
the one or more second regions are configured to transfer a greater amount of force than the one or more first regions.

16. The physiological sensing mat of claim 15, wherein the one or more second regions are positioned at individual sensors of the array of sensors.

17. The physiological sensing mat of claim 15, wherein the one or more second regions have a greater rigidity than the one or more first regions.

* * * * *